(12) United States Patent
Miller et al.

(10) Patent No.: US 7,122,794 B1
(45) Date of Patent: *Oct. 17, 2006

(54) SYSTEMS AND METHODS FOR ION MOBILITY CONTROL

(75) Inventors: Raanan A. Miller, Chestnut Hill, MA (US); Clayton James Morris, Norfolk, MA (US); Douglas B. Cameron, Wellesley, MA (US); Erkinjon G. Nazarov, Lexington, MA (US); John A. Wright, Billerica, MA (US)

(73) Assignee: Sionex Corporation, Bedford, MA (US)

( * ) Notice: Subject to any disclaimer, the term of this patent is extended or adjusted under 35 U.S.C. 154(b) by 30 days.

This patent is subject to a terminal disclaimer.

(21) Appl. No.: 10/903,497

(22) Filed: Jul. 30, 2004

Related U.S. Application Data

(63) Continuation-in-part of application No. 10/831,646, filed on Apr. 23, 2004, now abandoned, and a continuation-in-part of application No. 10/462,206, filed on Jun. 13, 2003, which is a continuation-in-part of application No. 10/321,822, filed on Dec. 16, 2002, now Pat. No. 6,806,463, and a continuation-in-part of application No. 10/082,803, filed on Feb. 21, 2002, now Pat. No. 6,815,669.

(60) Provisional application No. 60/504,024, filed on Sep. 20, 2003, provisional application No. 60/491,443, filed on Jul. 31, 2003, provisional application No. 60/483,001, filed on Jun. 27, 2003, provisional application No. 60/468,306, filed on May 6, 2003, provisional application No. 60/464,977, filed on Apr. 24, 2003.

(51) Int. Cl.
*B01D 59/44* (2006.01)
*H01J 49/00* (2006.01)
*H01J 49/40* (2006.01)

(52) U.S. Cl. ............... 250/294; 250/281; 250/282; 250/292; 250/293

(58) Field of Classification Search ........ 250/281–288, 250/290, 292–294
See application file for complete search history.

(56) References Cited

U.S. PATENT DOCUMENTS

| | | |
|---|---|---|
| 2,615,135 A | 10/1952 | Glenn |
| 2,818,507 A | 12/1957 | Britten |
| 2,919,348 A | 12/1959 | Blerman |
| 3,511,986 A | 5/1970 | Llewellyn |
| 3,619,605 A | 11/1971 | Cook et al. |
| 3,621,240 A | 11/1971 | Cohen et al. |
| 3,931,589 A | 1/1976 | Aisenberg et al. |
| 4,019,989 A | 4/1977 | Hazewindus et al. |
| 4,025,818 A | 5/1977 | Giguere et al. |
| 4,136,280 A | 1/1979 | Hunt et al. |

(Continued)

FOREIGN PATENT DOCUMENTS

RU 1412447 A1 6/1998

(Continued)

OTHER PUBLICATIONS

Krylov, E.V., "Comparison of the Planar and Coaxial Field Asymmetrical Waveform Ion Mobility Spectrometer (FAIMS)," International Journal of Mass Spectrometry, 225, (2003) pp. 39-51.

(Continued)

*Primary Examiner*—John R. Lee
*Assistant Examiner*—Bernard E. Souw
(74) *Attorney, Agent, or Firm*—Fish & Neave IP Group Ropes&Gray LLP

(57) ABSTRACT

The invention provides, in various embodiments, systems and methods relating to controlling ion behavior in an ion-based analysis system.

42 Claims, 23 Drawing Sheets

U.S. PATENT DOCUMENTS

| | | | |
|---|---|---|---|
| 4,163,151 A | 7/1979 | Bayless et al. | |
| 4,201,921 A | 5/1980 | McCorkle | |
| 4,315,153 A | 2/1982 | Vahrenkamp | |
| 4,517,462 A | 5/1985 | Boyer et al. | |
| 4,761,545 A | 8/1988 | Marshall et al. | |
| 5,144,127 A | 9/1992 | Williams et al. | |
| 5,218,203 A | 6/1993 | Eisele et al. | |
| 5,298,745 A | 3/1994 | Kernan et al. | |
| 5,420,424 A | 5/1995 | Carnahan et al. | |
| 5,455,417 A | 10/1995 | Sacristan | |
| 5,492,867 A | 2/1996 | Kotvas et al. | |
| 5,536,939 A | 7/1996 | Freidhoff et al. | |
| 5,541,408 A | 7/1996 | Sittler | |
| 5,654,544 A | 8/1997 | Dresch | |
| 5,723,861 A | 3/1998 | Carnahan et al. | |
| 5,763,876 A | 6/1998 | Pertinarides et al. | |
| 5,789,745 A | 8/1998 | Martin et al. | |
| 5,801,379 A | 9/1998 | Kouznetsov | |
| 5,811,059 A | 9/1998 | Genovese et al. | |
| 5,834,771 A | 11/1998 | Yoon et al. | |
| 5,838,003 A | 11/1998 | Bertsch et al. | |
| 5,965,882 A | 10/1999 | Megerle et al. | |
| 5,998,788 A | 12/1999 | Breit | |
| 6,051,832 A | 4/2000 | Bradshaw | |
| 6,055,151 A | 4/2000 | Tormey et al. | |
| 6,066,848 A | 5/2000 | Kassel et al. | |
| 6,107,624 A | 8/2000 | Doring et al. | |
| 6,107,628 A | 8/2000 | Smith et al. | |
| 6,124,592 A | 9/2000 | Spangler | |
| 6,200,539 B1 | 3/2001 | Sherman et al. | |
| 6,323,482 B1 | 11/2001 | Clemmer et al. | |
| 6,479,815 B1 | 11/2002 | Goebel et al. | |
| 6,495,823 B1 * | 12/2002 | Miller et al. | 250/286 |
| 6,504,149 B1 | 1/2003 | Guevremont et al. | |
| 6,512,224 B1 | 1/2003 | Miller et al. | |
| 6,621,077 B1 | 9/2003 | Guevremont et al. | |
| 6,639,212 B1 | 10/2003 | Guevremont | |
| 6,653,627 B1 | 11/2003 | Guevremont | |
| 6,690,004 B1 | 2/2004 | Miller et al. | |
| 6,703,609 B1 | 3/2004 | Guevremont | |
| 6,713,758 B1 | 3/2004 | Guevremont | |
| 6,753,522 B1 | 6/2004 | Guevremont | |
| 6,770,875 B1 | 8/2004 | Guevremont | |
| 6,774,360 B1 | 8/2004 | Guevremont | |
| 6,787,765 B1 | 9/2004 | Guevremont | |
| 6,791,078 B1 * | 9/2004 | Giles et al. | 250/286 |
| 6,799,355 B1 | 10/2004 | Guevremont | |
| 6,806,463 B1 * | 10/2004 | Miller et al. | 250/286 |
| 6,806,466 B1 | 10/2004 | Guevremont | |
| 6,815,669 B1 * | 11/2004 | Miller et al. | 250/286 |
| 2001/0030285 A1 | 10/2001 | Miller et al. | |
| 2002/0070338 A1 | 6/2002 | Lododa | |
| 2002/0134932 A1 | 9/2002 | Guevremont et al. | |
| 2003/0020012 A1 | 1/2003 | Guevremont | |
| 2003/0038235 A1 | 2/2003 | Guevremont et al. | |
| 2003/0052263 A1 | 3/2003 | Kaufman et al. | |
| 2003/0089847 A1 | 5/2003 | Guevremont et al. | |
| 2003/0132380 A1 | 7/2003 | Miller et al. | |
| 2004/0094704 A1 * | 5/2004 | Miller et al. | 250/287 |

FOREIGN PATENT DOCUMENTS

| | | |
|---|---|---|
| RU | 1485808 A1 | 6/1998 |
| SU | 966583 A | 10/1982 |
| SU | 1337934 A2 | 9/1987 |
| SU | 1627984 A2 | 2/1991 |
| WO | WO-96/19822 A1 | 6/1996 |
| WO | WO-00/08454 | 2/2000 |
| WO | WO-00/08455 | 2/2000 |
| WO | WO-00/08456 | 2/2000 |
| WO | WO-00/08457 | 2/2000 |
| WO | WO-01/08197 A1 | 2/2001 |
| WO | WO-01/22049 A2 | 3/2001 |
| WO | WO-01/35441 A1 | 5/2001 |
| WO | WO-01/69217 A2 | 9/2001 |
| WO | WO-01/69220 A2 | 9/2001 |
| WO | WO-01/69647 A2 | 9/2001 |
| WO | WO-02/071053 A2 | 9/2002 |
| WO | WO-02/083276 | 10/2002 |
| WO | WO-03/005016 | 1/2003 |
| WO | WO-2003/015120 | 2/2003 |
| WO | WO 2004/097396 A1 * | 11/2004 |
| WO | WO 2006/015305 A2 * | 2/2006 |

OTHER PUBLICATIONS

"A Micromachined Field Driven Radio Frequency-Ion Mobility Spectrometer for Trace Level Chemical Detection," A Draper Laboratory Proposal Against the "Advanced Cross-Enterprise Technology Development for NASA Missions," Solicitation, NASA NRA 99-OSS-05.

Barnett et al., "Isotope Separation Using High-Field Asymmetric Waveform Ion Mobility Spectrometry," Nuclear Instruments & Methods in Physics Research, vol. 450, No. 1, pp. 179-185 (2000).

Buryakov et al., "A New Method of Separation of Multi-Atomic Ions by Mobility at Atmospheric Pressure Using a High-Frequency Amplitude-Asymmetric Strong Electric Field," International Journal of Mass Spectrometry and Ion Processes, vol. 128, pp. 143-148 (1993).

Buryakov et al., "Drift Spectrometer for the Control of Amine Traces in the Atmosphere," J. Anal. Chem., vol. 48, No. 1, pp. 112-121 (1993).

Buryakov et al., "Separation of Ions According to Mobility in a Strong AC Electric Field," Letters to Journal of Technical Physics, vol. 17, pp. 11-12 (1991).

Buryakov et al., "Device and Method for Gas Electrophoresis, Chemical Analysis of Environment," ed. Prof. V.V. Malakhov, Novosibirsk: Nauka, pp. 113-127 (1991).

Carnahan et al., "Field Ion Spectrometry—A New Analytical Technology for Trace Gas Analysis," ISA, vol. 51, No. 1, pp. 87-96 (1996).

Carnahan et al., "Field Ion Spectrometry—A New Technology for Cocaine and Heroin Detection," SPIE, vol. 2937, pp. 106-119 (1997).

EICEMAN et al., "Miniature radio-frequency mobility analyzer as a gas chromatogrphic detector for oxygen-containing volatile organic compounds, pheromones and other insect attractants," Journal of Chromatography, vol. 917, pp. 205-217 (2001).

Guevremont et al., "Atmospheric Pressure Ion Focusing in a High-Field Asymmetric Waveform Ion Mobility Spectrometer," Review of Scientific Instruments, vol. 70, No. 2, pp. 1370-1383 (1999).

Guevremont et al., "Calculation of Ion Mobilities from Electrospray Ionization High-Field Asymmetric Waveform Ion Mobility Spectrometry Mass Spectrometry," Journal of Chemical Physics, vol. 114, No. 23, pp. 10270-10277 (2001).

Guevremont et al., "High Field Asymmetric Waveform Ion Mobility Spectrometry-Mass Spectrometry: An Investigation of Leucine Enkephalin Ions Produced by Electrospray Ionization," J. Am. Soc. Mass. Spectrom., vol. 10, pp. 492-501 (1999).

Handy et al., "Determination of Nanomolar Levels of Perchlorate in Water by ESI-FAIMS-MS," J. Anal. At. Spectrometry, vol. 15, pp. 907-911 (2000).

Javahery et al., "A segmented radiofrequency-only quadrupole collision cell for measurements of ion collision cross section on a triple quadrupole mass spectrometer," J. Am. Soc. Mass. Spectrom. 8:697-702 (1997).

Krylov, "A Method of Reducing Diffusion Losses in a Drift Spectrometer," Technical Physics, vol. 4d, No. 1, pp. 113-116 (1999).

Krylov, "Pulses of Special Shapes Formed on a Capacitive Load," Instruments and Experimental Techniques, vol. 40, No. 5, (1997). Also cited in Database Nauka/Interperiodika 'Online!, International Academic Publishing Company (IAPC), Russia, E. Krylov.

Miller et al., "A MEMS Radio-Frequency Ion Mobility Spectrometer for Chemical Agent Detection," Proceedings of the 2000 Solid State Sensors and Actuators Workshop (Hilton Head, SC, Jun. 2000).

Miller et al., "A MEMS radio-frequency ion mobility spectrometer for chemical vapor detection," Sensors and Actuators, vol. 91, pp. 301-312 (2001).

Miller et al., "A Novel Micromachined High-Field Asymmetric Waveform-Ion Mobility Spectrometer," Sensors and Actuators B, vol. B67, No. 3, pp. 300-306 (2000).

Pilzecker et al., "On-Site Investigations of Gas Insulated Substations Using Ion Mobility Spectrometry for Remote Sensing of SF6 Decomposition," IEEE, pp. 400-403 (2000).

Riegner et al., "Qualitative Evaluation of Field Ion Spectrometry for Chemical Warfare Agent Detection," Proceedings of the ASMS Conference on Mass Spectrometry and Allied Topics, pp. 473A-473B (1997).

Schneider et al., "High Sensitivity GC-FIS for Simultaneous Detection of Chemical Warfare Agents," Journal of Process Analytical Chemistry, vol. 5, Nos. 3, 4, pp. 124-136 (2000).

Verenchikov et al., "Analysis ions in solutes by gaseous ion analyzer—chemical analysis of the environmental objects," red. Malakhov. Novosibirsk, Nauka pp. 127-134 (1991).

* cited by examiner

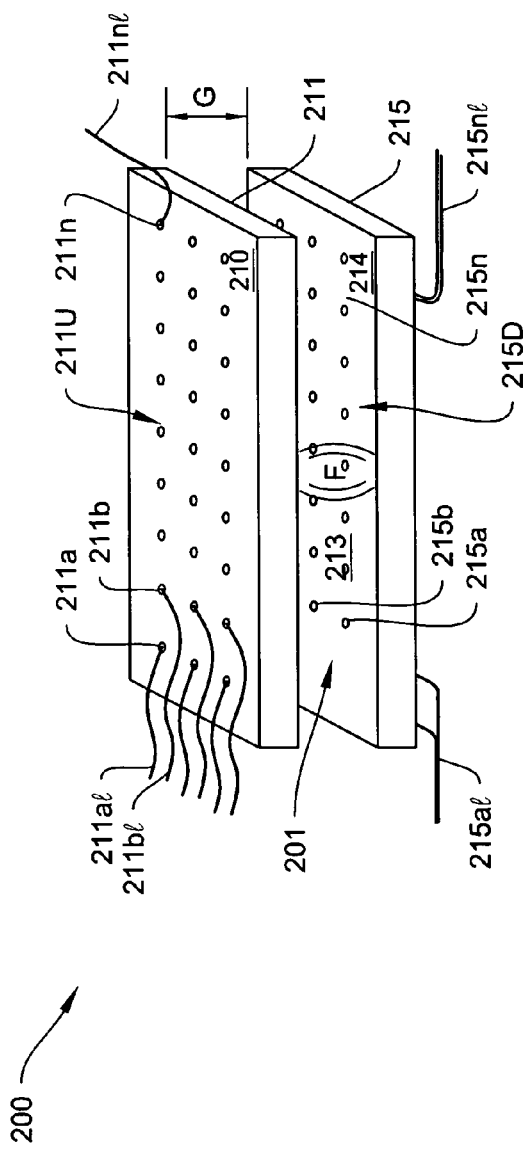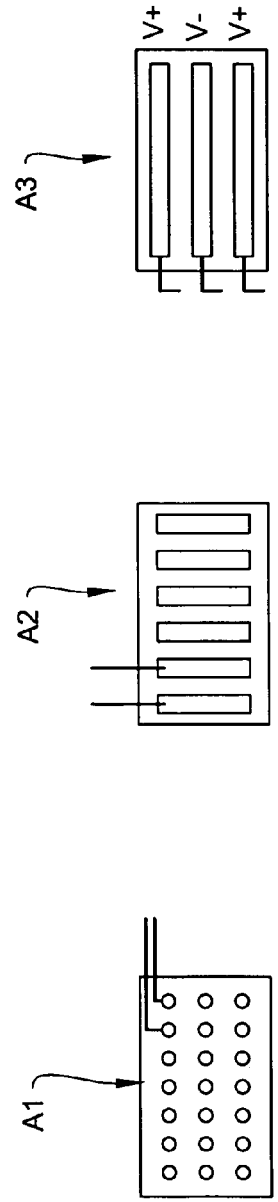
FIG. 4A
FIG. 4B
FIG. 4C
FIG. 4D

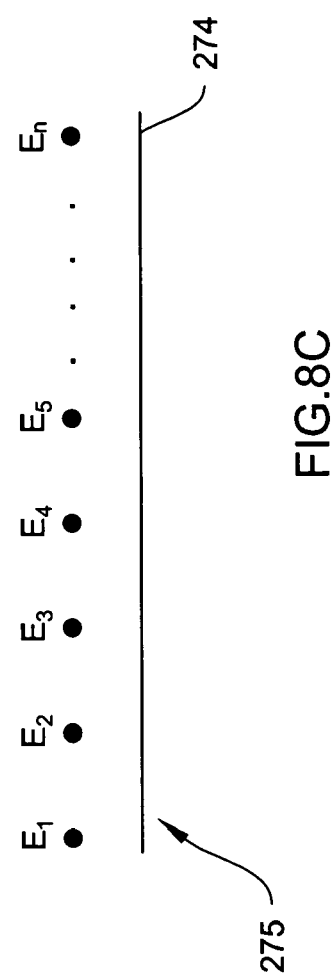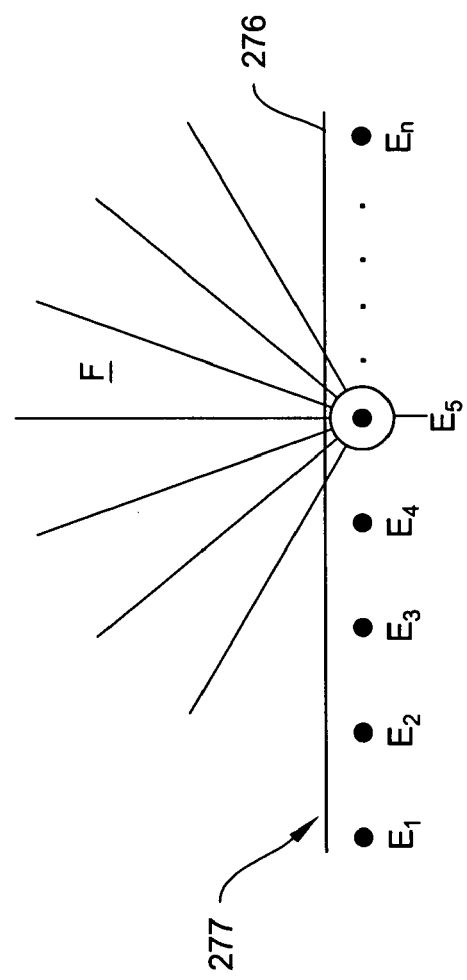
FIG.8C
FIG.8D

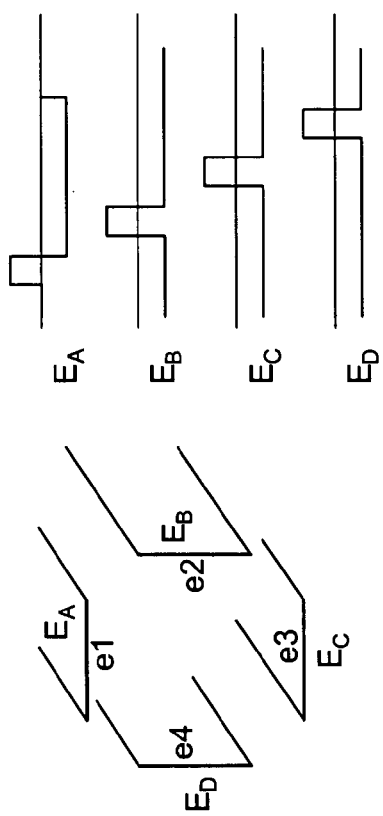
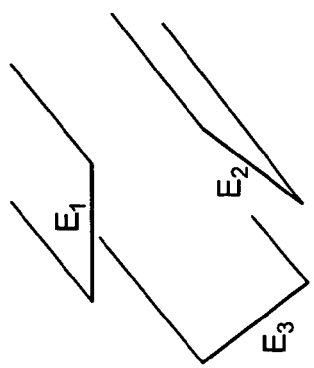
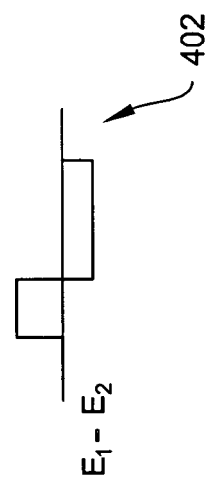
FIG. 9C
FIG. 9E
FIG. 9D

SYSTEMS AND METHODS FOR ION MOBILITY CONTROL

REFERENCE TO RELATED APPLICATIONS

This application is a continuation-in-part of U.S. application Ser. No. 10/831,646, filed Apr. 23, 2004 now abandoned, which is a continuation-in-part of U.S. application Ser. No. 10/321,822, filed Dec. 16, 2002 now U.S. Pat. No. 6,806,463, and of U.S. application Ser. No. 10/082,803, filed Feb. 21, 2002 now U.S. Pat. No. 6,815,669, and of U.S. application Ser. No. 10/462,206, filed Jun. 13, 2003, and claims the benefit of U.S. Provisional Application No. 60/464,977, filed on Apr. 24, 2003, U.S. Provisional Application No. 60/483,001, filed on Jun. 27, 2003, U.S. Provisional Application No. 60/468,306, filed May 6, 2003, U.S. Provisional Application No. 60/491,443, filed on Jul. 31, 2003, and U.S. Provisional Application No. 60/504,024, filed on Sep. 20, 2003. The entire teachings of the above applications are incorporated herein by reference.

FIELD OF THE INVENTION

This invention relates to methods and apparatus for detecting ions based on aspects of ion mobility behavior.

BACKGROUND

Several approaches to chemical identification are based on the recognition that ion species have different ion mobility characteristics under different electric field conditions at atmospheric pressure. These approaches include time-of-flight Ion Mobility Spectrometry (IMS) and differential mobility spectrometry (DMS), the latter also known by other names such as field asymmetric ion mobility spectrometry (FAIMS). Atmospheric-pressure chemical ionization enables these identification processes (including radioactive, ultraviolet and electrospray ionization, for example).

In a conventional IMS device, a weak DC field gradient is established between an upstream electrode and a downstream collector electrode and then an ionized sample is released into the DC field. The ionized sample flows toward the collector electrode. Ion species are identified based on the time of flight of the ions to the collector. The DC field is weak where ion mobility is constant.

A typical DMS device includes a pair of opposed filter electrodes defining an analytical gap between them in a flow path (also known as a drift tube or flow channel). Ions flow into the analytical gap. A compensated high-low varying asymmetric RF field (sometimes referred to as a filter field, a dispersion field or a separation field) is generated between the electrodes transverse the ion flow in the gap. Field strength varies as the applied RF voltage (sometimes referred to as dispersion voltage, separation voltage, or RF voltage) and size of the gap between the electrodes. Such systems typically operate at atmospheric pressure.

Ions are displaced transversely by the DMS filter field, with a given species being displaced a characteristic amount transversely toward the electrodes per cycle. DC compensation is applied to the electrodes to compensate or offset the transverse displacement generated by the applied RF for a selected ion species. The result is zero or near-zero net transverse displacement for that species, which enables that species to pass through the filter for downstream processing such as detection and identification. Other ions undergo a net transverse displacement toward the filter electrodes and will eventually undergo collisional neutralization on one of the electrodes.

SUMMARY OF THE INVENTION

Systems and methods of the invention generally relate to processing a sample in an ion flow path of a chemical analyzer. In various embodiments, the processing includes ion filtering and/or ion separating. In various other embodiments, the invention also includes ion species detection and identification.

Ion behavior within the flow path of an ion-based chemical analysis device can be controlled and manipulated to improve or even optimize system performance. Practices of the invention include using control structures to improve DMS ion species analysis. These control surfaces are variously employed for dissipating charge and/or for forming a controlling electric field.

In one practice of the invention, an influencing structure and/or an influencing field influences the analytical environment within the analyzer such as to enhance stability of the analyzer. According to one feature, the influencing structure and field counteracts or overcomes various local effects that impact ion behavior. According to other features, the invention enables stabilizing ion analysis, as well as enabling focusing, trapping, confining, translating, selecting, steering, concentrating and/or filtering ions in the flow path of an ion mobility-based analytical system, such as an IMS or DMS system.

In one embodiment, the invention is integrated into a DMS system, which may be a spectrometer, filter, detector, separator, assembly, apparatus or the like. A flow path is defined that enables ionized sample to flow into the analytical gap defined between facing DMS filter electrodes in the flow path. Ion species are separated in the filter field and selected species are passed for downstream processing, such as for detection and identification, according to ion behavior in the compensated asymmetric RF filter field. Ion control is exercised within such device. In a further embodiment, the RF field is not compensated and ion control is implemented at control surfaces of the flow path.

In one embodiment, a control material in the flow path provides charge dissipating surfaces or structures that prevent or control charge buildup as impacts ion behavior in the system. In such embodiment, this material provides a discharge path for charges deposited on such surfaces, reducing or eliminating surface charges in the flow path, to control effect upon or interaction with the intended ion analysis.

In another embodiment, we provide active control structures for controlling various fields, artifacts, or the like, such as fringing effects at the filter electrode edges. In another embodiment, we achieve ion control (such as focusing or concentrating ions by field control), wherein electrodes, such as a grid or array of electrodes, are driven to selectively generate a non-uniform field. The non-uniform field is used to position ions in the ion flow. This positioning may include focusing and/or concentrating all ions in a flow to a specific flow path location or into a specific flow profile, or may include concentrating only a selection of ions in the flow which separate from other ions in the flow. This same set of electrodes can be driven to gate ion flow, such as for time of flight analysis.

The invention has other aspects, such as enabling ion steering and ion flow compensation, including selective changes of ion flow from one flow path to another flow path. This innovation may be placed within one device or may assist coupling from one system to another system (e.g., from a DMS to a mass spectrometer).

In a further embodiment, the flow path includes control surfaces in contact with a plurality (i.e., an array, grid, or set)

of control electrodes. This "control array" may passively (e.g., by using a dissipative surface) or actively (e.g., by applying a control field) affect ion behavior in the flow path. This control function may be performed along a flow path structure, layer, surface, covering, coating, substrate, region, or the like.

In several embodiments, the invention employs a control structure that is generally described herein as "partially conducting", which refers to having some capacity to conduct a charge, but without impairing function of neighboring electrodes. This control structure may also include use of a plurality of control elements whose combined effect is to be partially conducting, although individual elements may be fully conductive.

In a charge dissipating embodiment of the invention, the overall effect of being "partially conducting" can be understood in the sense of being conductive enough to enable bleeding off or neutralizing of charge as it is being built-up on flow path surfaces but sufficiently resistive so as to be able to support a voltage gradient. Charge build-up can interfere with stability of an ion-based analytical system and therefore removal of the effect of charge buildup is a benefit of an embodiment of the invention.

Partially conducting material may include resources such as semiconductor material, resistive paint, doped glass, use of ion implantation, or the like applied to a substrate. The resistance of the material overall may be governed by selected geometry and voltage, as well as material properties. In various embodiments of the invention, a range of resistance is about $10^2 \leq$ ohms/square $\leq$ about $10^{14}$, and in other embodiments, is within a range of about $10^7 \leq$ ohms/square $\leq$ about $10^{11}$.

In one practice of the invention, a DMS device has a structure that defines a flow path. The flow path includes facing partially conducting layers of control material with a plurality of control electrodes to form facing control arrays. The control arrays are addressed and driven to control motion of ions in the flow path. Such control layers enable conveying, controlling, separating, neutralizing, processing, and/or passing, selected ions and ion species. These arrays can provide the filter electrode function or can be isolated from the ion filter electrodes. These arrays may be used for charge dissipation as well as other ion flow control and separation functions.

According to various embodiments of the systems and methods for controlling ion behavior in an ion-based analysis system, described herein, the control can be static or dynamic, such as by supplying a constant or time-varying field. One embodiment includes an ion source, an ion flow path, an ion controller including surfaces facing the flow path, an ion filter including electrodes separated by an analytical gap, and a control system for controlling ion behavior between various electrodes. In one example, the control system generates at least one electric field, for example, for concentrating ions in the flow path, and/or increasing or decreasing density of particular ions in the flow path. In another embodiment, the concentrated ions are filtered according to ion-mobility-based behavior in the filter. Some advantages of achieving this level of field control are improved ion flow behavior, higher ion filtering efficiency and increased detection capabilities. Thus, in various embodiments, the systems and methods of the invention provide better sensitivity, higher resolution and better performance for an ion-mobility based analytical device.

The following description sets forth details of various illustrative advantages, features, implementations and applications of the invention. More particularly, the illustrative embodiments of the invention are described with regard to a DMS device, a mass producible DMS chip assembly, and further innovations in ion control in a DMS device. It should be noted that the systems and methods of the invention are not limited to DMS applications, and that these descriptions are by way of illustration only and not intended to limit the scope of the invention.

BRIEF DESCRIPTION OF THE DRAWINGS

The foregoing and other objects, features and advantages of the invention will be apparent from the following illustrative description, along with the accompanying drawings, in which like reference characters refer to the same parts throughout the different views. The drawings are not necessarily to scale, emphasis instead being placed on illustrating the principles of the invention.

FIG. 4A is a side perspective view of a pair of partially conducting control material layers according to an illustrative embodiment of the invention.

FIGS. 4B–4D show electrode configurations according to illustrative embodiments of the invention.

FIGS. 8A–8D show alternative field effects according to illustrative embodiments of the invention.

FIG. 9A shows concentrator electrodes in practice of the invention.

FIGS. 9B–9E show concentrator electrodes and drive signals according to illustrative embodiments of the invention.

ILLUSTRATIVE DESCRIPTION

The invention, in various illustrative embodiments, enables improved ion mobility-based chemical analysis. One embodiment includes DMS ion species separation, detection and identification. The invention may be practiced with various systems where ion control is useful. One illustrative embodiment is implemented in a DMS chemical ionizer.

In practices of the invention, a DMS system receives a sample in a fluid flow, filters the ionized fluid flow, and passes ion species of interest for downstream processing. According to one practice, the ions are carried by a gas stream (sometimes referred to as a carrier gas) through stages of the system (e.g., into a DMS filter and toward a detector), as taught in U.S. Pat. No. 6,495,823, incorporated herein by reference. Alternatively, the sample may be conveyed via an electric propulsion field, with or without carrier gas, as taught in U.S. Pat. No. 6,512,224, also incorporated herein by reference.

Illustrative DMS Assembly

Figure 1:
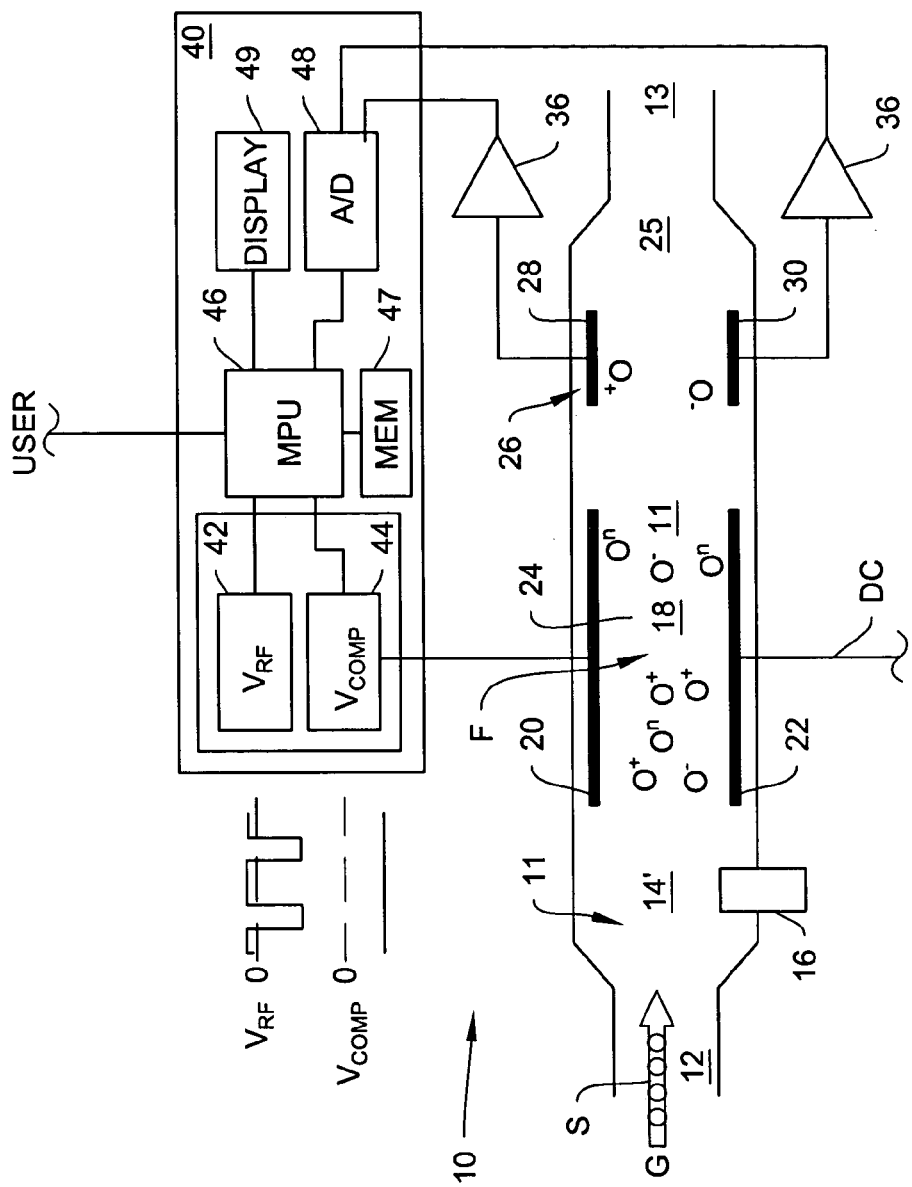
FIG. 1 is a schematic of a field asymmetric ion mobility spectrometer.

In an illustrative DMS assembly 10, as shown in FIG. 1, flow path 11 has inlet 12 for receipt of carrier gas flow G carrying sample S into the device. The sample is drawn from the environment or received from a front-end device, such as a gas chromatograph (GC), and flows from inlet 12 to ionization region 14 along the flow path 11.

Compounds in the sample are ionized by an ionization source 16 as the sample flows through ionization region 14, creating a set of ionized molecules ++,-- accompanied by some neutral molecules n, of various chemical species. According to one embodiment, ionized monomers and/or dimers, etc. are created during such ionization. Also, clusters of ions may be created when a monomer combines with water molecules or other background molecules.

In the embodiment of FIG. 1, carrier gas G carries the ions into analytical gap 18 (e.g., 0.5 mm) between filter electrodes 20 and 22 of ion filter 24. A compensated asymmetric RF filter field F is developed between the ion filter electrodes in the analytical gap. The strength of the field varies according to the applied RF voltage ($V_{RF}$). The RF field may be compensated, such as by application of a DC offset (Vcomp). Compensation may also be implemented by varying other aspects of the filter field, and is applied on a species-specific basis.

A detector 26 is incorporated into system 10, and takes the form of at least one electrode, and preferably includes a plurality of electrodes, such as, without limitation, opposed electrodes 28 and 30, associated with the flow path downstream of filter 24. However, alternatively, systems of the invention may include detecting the filter output with a mass spectrometer (MS) or other external detection system. In one embodiment, the invention improves species separation as a front-end device to enhance MS detection.

Control unit 40 performs a number of important actions in accordance with the invention, and may incorporate various devices or functions for this purpose. These may include RF voltage generator 42, an optional compensation voltage generator 44, a microprocessor unit (MPU) 46, memory 47, an analog-to-digital (A/D) converter 48, and display 49.

The microprocessor 46 provides digital control signals to the RF voltage generator 42 and the compensation voltage generator 44 to generate the desired compensated drive voltages for the filter 24. These devices may also include digital-to-analog (D/A) converters and the like, although not shown in detail. In the embodiment of FIG. 1, the control unit 40 biases and monitors the electrodes 28 and 30 of the detector 26. The microprocessor 46 correlates applied compensation and RF voltages with observed responses at the detector 26, via the analog-to-digital (A/D) converter 48. Matching of this detection data against stored detection data in the memory 47 enables identification of detected species. The system may be preprogrammed or may accommodate intervention by a "user".

According to various illustrative embodiments of the invention, applied peak RF voltages can range from less than about 1,000 V/cm to about 30,000 V/cm. The frequency may range from less than about 1 MHz to beyond about 20 MHz, depending upon species. In one embodiment, a duty cycle of about 30% is employed at higher frequencies for good effect, although other operating ranges, voltages, field strengths, duty cycles, wavelengths and frequencies may be employed in other illustrative embodiments of the invention.

In a DMS, ions are separated based on mobility differences in the filter field F in the analytical gap 18 according to the filter field conditions. Field F can be held at a fixed periodic value, where the system is dedicated to detecting particular ion species at a single data point, or the field conditions can be varied for generating a plurality of data points.

Additionally, at least one field parameter (such as DC compensation or RF duty cycle) can be scanned to generate a mobility scan. The field conditions are set to a particular value, except for at least one of such mobility-affecting parameters, which is swept through a range to generate a mobility spectrum for the sample under test. According to the illustrative embodiment, this is performed under direction and control of the control unit 40.

Figure 2A:
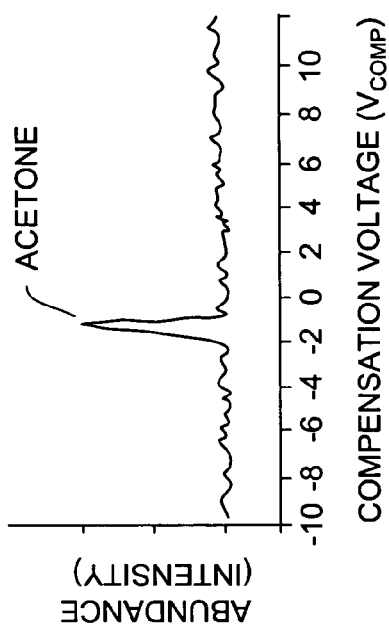
FIGS. 2A–2B show mobility scans plotting detection intensity versus compensation voltage for a given field strength in a DMS, for acetone alone, FIG. 2A, and for a combination of o-xylene and acetone, FIG. 2B.
Figure 2B:
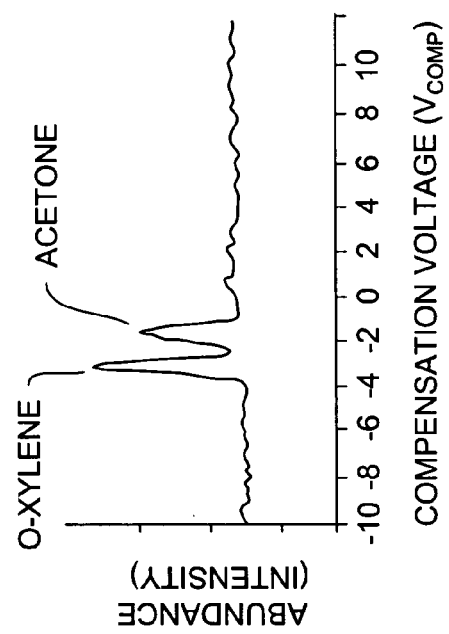

Illustrative examples of mobility scans based on the output from a DMS device are shown in FIGS. 2A–2B. In FIG. 2A a single compound, acetone, was submitted to a DMS analyzer. The illustrated plot is typical of the observed response of the DMS device, with detected acetone ions in this example forming a peak intensity at a compensation voltage of about –1.5 volts. This is useful information, such that future detections of a peak at this compensation in this device is indicative of acetone detection.

In FIG. 2B, the analyzed sample consisted of acetone and an isomer of xylene (o-xylene). FIG. 2B demonstrates unique detection peaks according to ion mobility characteristics for the different ion species, o-xylene and acetone. The acetone peak appears at about –2.5 volts while o-xylene appears at about –4 volts. Data representing these detection peaks can be compared against stored data for known compounds for this device and the applied RF field and compensation, and identification is made based upon a data match.

As can be seen, the above-described system 10 of the invention provides a stable DMS device capable of repeatable test results. In one practice, the invention uses a library of information for identifying detected species, in view of compensation, RF and other field conditions. It is also within the scope of the invention to calibrate the system using the reactant ion peak (RIP) and/or a dopant peak, for example, among other techniques.

Mass Producible DMS Chip Assembly

Figure 3A:
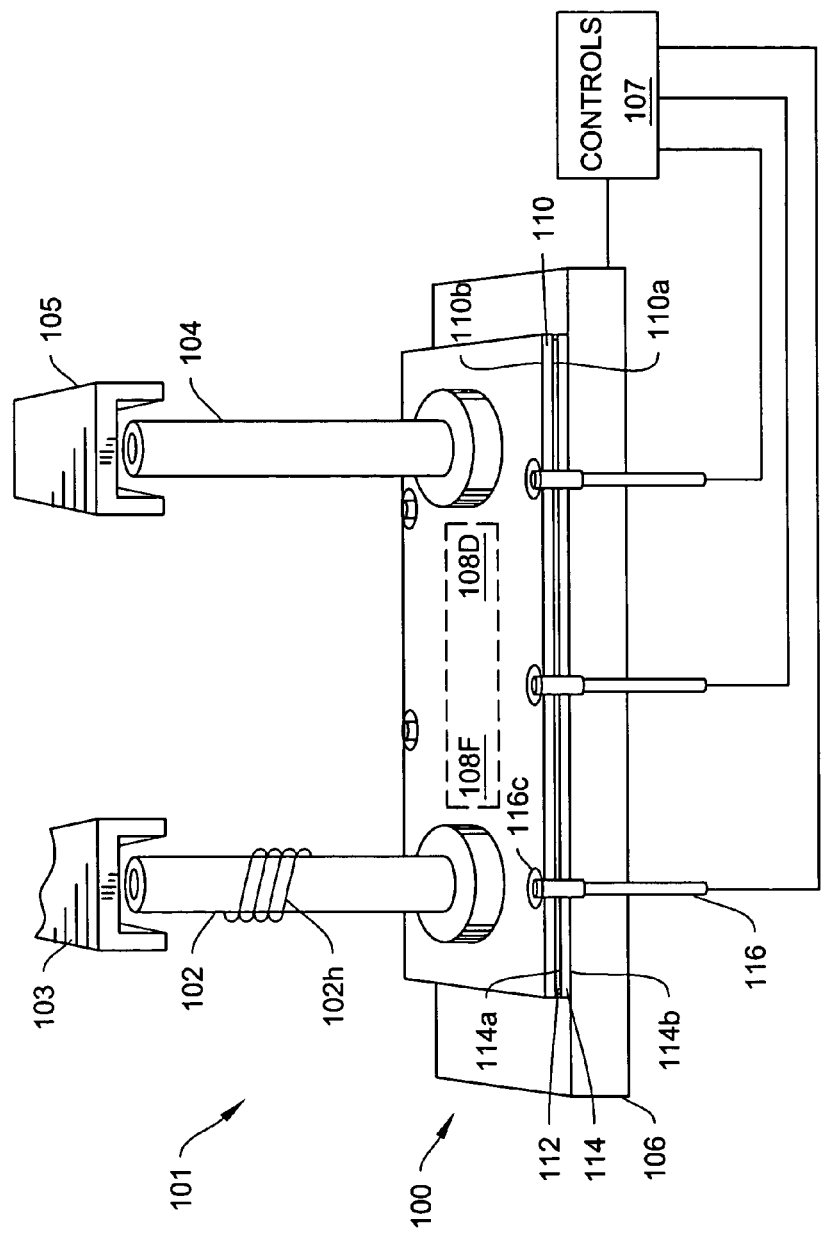
FIG. 3A is a side perspective view of a DMS embodiment of the invention.

A mass producible DMS chip 100, formed into an analytical assembly 101, is shown in FIG. 3A. In an exemplary embodiment, chip 100 includes components shown in FIGS. 3B–3D. Assembly 101 performs an I/O function, a processing function, and a control function. According to the embodiment depicted by FIG. 3A, the I/O function includes an inlet tube 102 for receipt of a gas sample from the environment (or from a GC output 103 or the like), and an outlet tube 104, which may be coupled to a pump 105 for exhaust of gas flow. (While inlet and outlet tubes are shown, alternative passages, pathways, orifices, openings, apertures, or other mechanisms of connection, ingress and egress, are within the scope of the invention.)

Chip 100 is preferably mounted into socket 106, which may be a conventional DIP or a custom socket, for off-board connection of the chip, such as for communication with off-board drive and control electronics 107. Spectrometer system 101 functions in a manner similar to the system 10 described above, wherein the flowing sample is ionized and is filtered in the filter section preferably according to the DMS techniques.

An illustrative chip 100 includes filter 108F and detector 108D (indicated by dotted outline on the face of chip 100 in FIG. 3A). The system is controlled and ion detection signals are evaluated and reported by the controller section 107. Controller 107 may be on-board or off-board. According to this embodiment, the chip 100 has electrical connectors, such as leads 116, bonding pads 116c, or other connection arrangements, enabling connection to off-board systems, controls and the like.

Figure 3B:
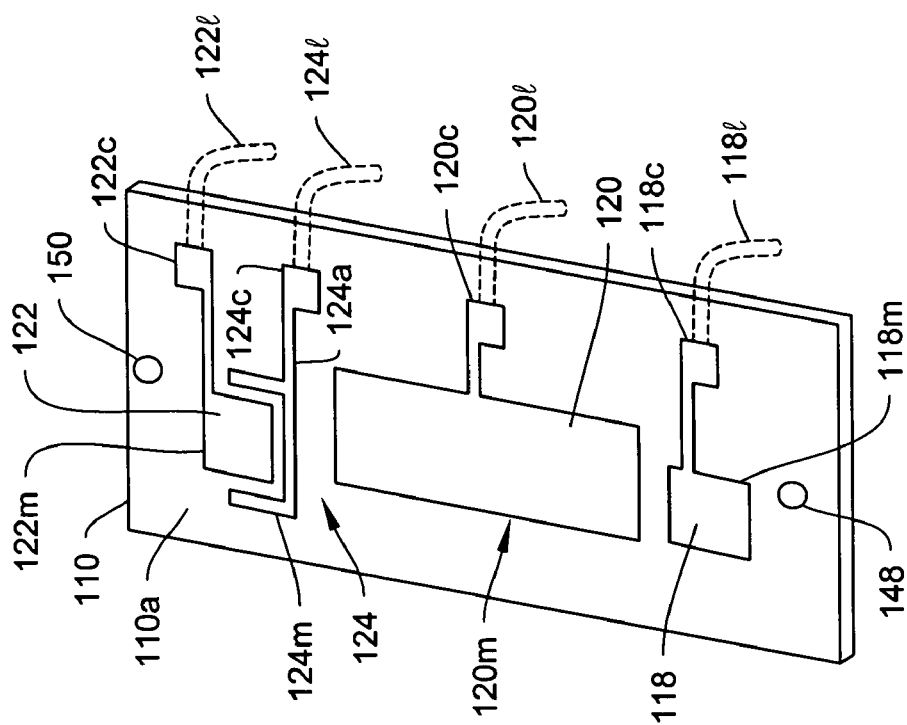
FIGS. 3B–3C are perspective views of substrates with electrodes in practice of the embodiment of FIG. 3A.
Figures 3C, 3D:
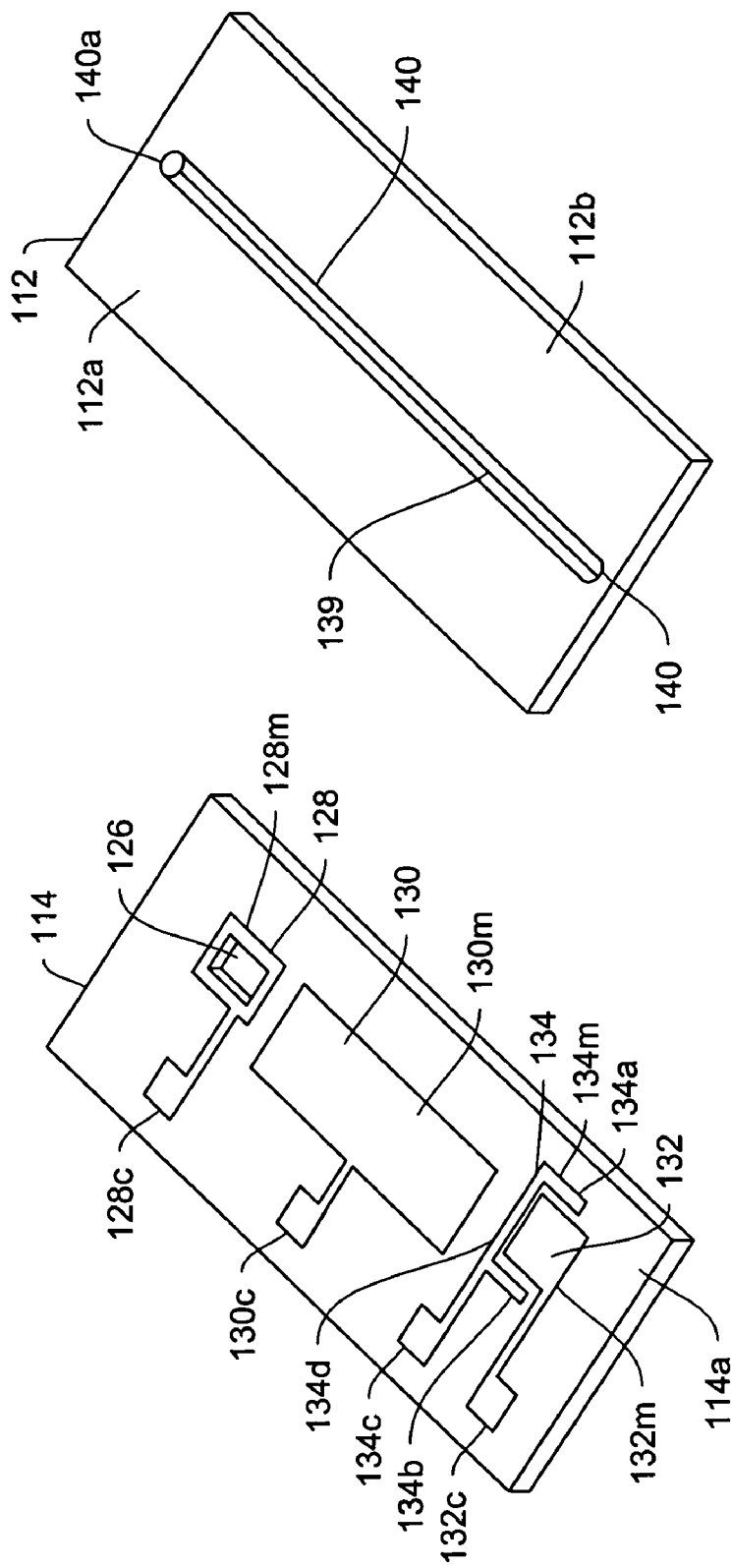
FIG. 3D is a perspective view of an exemplary spacer frame illustrative of the type that may be employed in the embodiment of FIG. 3A.
Figure 3E:
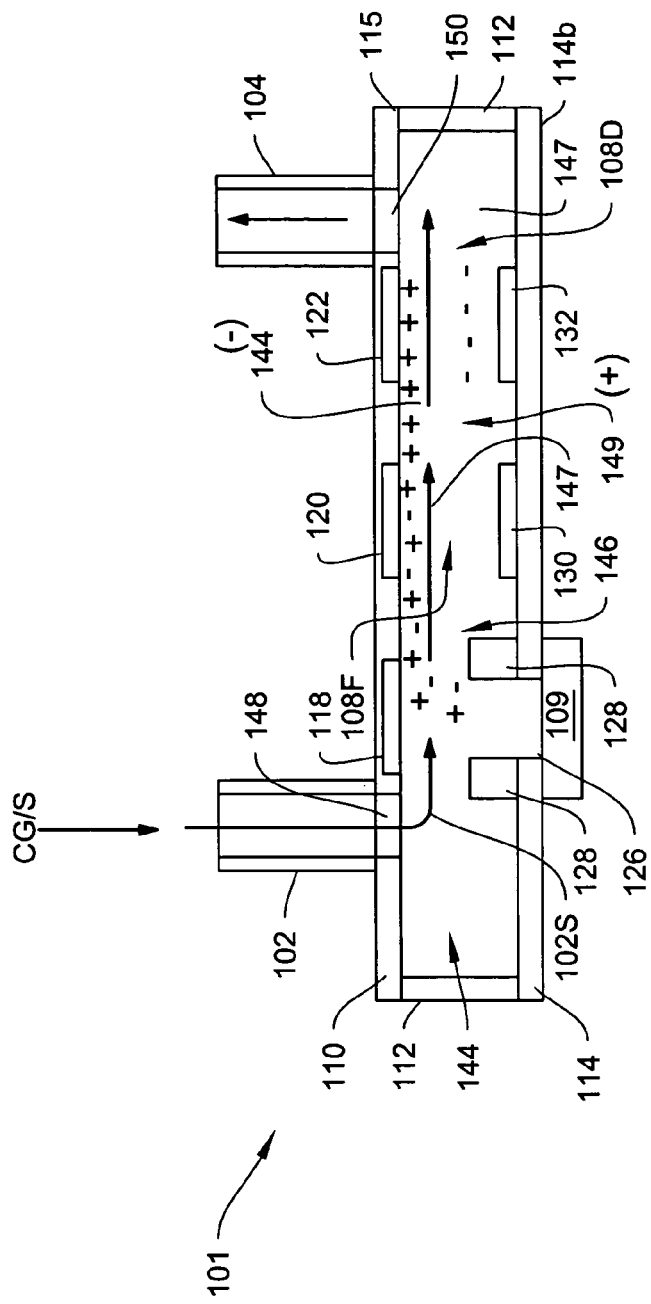
FIG. 3E is a side schematic view of a DMS device according to an illustrative embodiment of the invention.

According to one practice, the chip 100 includes substrate 110 (see FIGS. 3A and 3B) and substrate 114 (see FIGS. 3A and 3C). These substrates are separated by a spacer frame 112 (see FIGS. 3A and 3D). Substrates 110 and 114 and spacer frame 112 are sealed together to form an enclosed flow path (with an enclosed channel 140) while forming a sealed housing 115 (FIG. 3E). The inlet tube 102, outlet tube 104, ion source 109 and electrical leads 116 are mounted on the housing. In one embodiment, the inlet tube is provided with an optional heater 102h (FIG. 3A), for heating the sample input.

Ionization of chemical sample in practice of the invention may be achieved by various techniques. Ionization source 109 may be an ultraviolet photo-ionization lamp, a plasma or radioactive source, ESI arrangement, laser ionization, or the like, and provides a mixture of ions corresponding to chemicals in the gas sample. The ionized sample is then passed to ion filter 108F where the applied compensated RF field between the filter electrodes selects and enables a particular ion species to pass through the filter. Once through the filter, the ion species is detected in detector 108D. If the filter field is scanned, then a detection spectrum can be generated for the sample.

In the embodiment of FIG. 3E, an ionization source 109 is integrated into chip 100 to ionize the sample in the gas flow from inlet 102, which is drawn through the DMS filter 108F by pump 105, under direction of drive and control electronics 107, similar to the function described above for chemical sensor system 10.

In the embodiment of FIG. 3A, inlet tube 102 and outlet tube 104 are mounted to the back surface 110b of substrate 110. As shown in FIGS. 3B–3E, the inner surface 110a of substrate 110 and inner surface 114a of substrate 114 include metallization patterns for defining an illustrative DMS system. As shown in FIGS. 3A–3E, an illustrative system of the invention includes substrate 110 having first metallization portion 118m (FIG. 3B) that defines attraction electrode 118 and its extension that forms bonding pad 118c to which a lead 118l is attached. Substrate 110 further includes a second metallization portion 120m that defines filter electrode 120, and its extension that forms bonding pad 120c to which a lead 120l is attached. Substrate 110 also includes third metallization portion 122m that defines detector electrode 122 and its extension that forms bonding pad 122c to which a lead 122l is attached.

First substrate 110 includes fourth metallization portion 124m that defines shielding electrode 124 and its extension that forms bonding pad 124c (to which a lead 124l will be attached). Shielding electrode 124 further defines shield 124a which shields detector electrode 122 from the RF filter signals, thus reducing leakage between the ion filter 108F and detector electrode 122 of detector 108D, and thus reducing noise in the ion detection signal.

As shown in FIGS. 3C and 3E, ionization access port 126 (a via or through hole) is defined in either or both substrates to enable ionization sources 109 to interact with the sample. Source 109 is shown mounted on the back side 114b of substrate 114 in FIG. 3E.

As shown in FIG. 3C, the front side 114a of substrate 114 includes first metallization portion 128m, through which port 126 extends, and defines a guiding electrode 128 and its extension that forms bonding pad 128c to which a lead (not shown) is attached.

As shown in FIG. 3C, substrate 114 further includes second metallization portion 130m that defines filter electrode 130 and its extension that forms bonding pad 130c to which a lead can be attached. Substrate 114 also includes third metallization portion 132m that defines detector electrode 132 and its extension that forms bonding pad 132c to which a lead can be attached.

Substrate 114 of FIG. 3C also includes fourth metallization portion 134m that defines shielding electrode 134 and its extension that forms bonding pad 134c to which a lead can be attached. Segment 134m further defines shields 134a, 134b, 134d which shield detector electrode 132 from the filter signals, thus reducing leakage current between filter 108F and detector electrode 132 and thus reducing noise in the ion detection signal.

Spacer (or spacer frame) 112 is preferably a strip of insulating material (which itself may be semi-conductive or otherwise static or charge dissipative) with a central through-slot 139 that cooperates with the substrates 110, 114 to define the drift channel 140. The sides of drift channel 140 are contained within the spacer frame 112 extensions 112a and 112b. Substrate 110 is placed on one side of spacer 112 and substrate 114 is placed on the other side of spacer 112. The workpiece is processed to set and form a sealed structure.

Illustratively, this structure, shown in FIG. 3E, forms the basic chip assembly 100 and defines an enclosed and sealed flow path 144 with access for fluid introduction into the flow path. The flow path is accessed at one end 140a (as shown in FIG. 3D) of channel 140 by, and is in fluid communication with, inlet tube 102 mounted over port (or through hole) 148 in substrate 110. The flow path 144 is vented at the other end 140b (as shown in FIG. 3D) by, and is in fluid communication with, outlet tube 104 mounted over port (or through hole) 150 in substrate 110.

In operation, a carrier gas including a chemical sample (CG/S) to be detected, is introduced as flow 102s into flow path 144 via inlet tube 102, and then passes into ionization region 146 and is subjected to the ionization source 109. In one embodiment, source 109 emits ions that pass through port 126, guided by a bias applied to guiding electrode 128 (e.g., a positive bias for a positive ion) and attracted by attraction electrode 118 into the flowing sample 102s. The attraction electrode is driven by an attraction bias (e.g., a negative bias for a positive ion). The ions ionize compounds in sample flow 102s creating ions ("+","−") that are carried in the flow between electrodes 120, 130 of filter 108F, where the ions are subjected to the compensated high field asymmetric waveform ion mobility techniques (as described earlier), and filtered (selected) ions pass through the filter. Ion species are detected at electrodes 122, 132 of detector 108D. The carrier gas flow then vents from the flow path 144 at outlet 104.

The flow path 144 may be at, above or below ambient pressure. In some applications, the carrier gas and sample flow is generated by a higher pressure at the inlet, such as produced when eluting samples from a GC, and the sample is carried along the flow path thereby. In another application, the flow is generated by a pressure gradient at the detector, such as at the inlet of an MS and the gas is drawn thereby. As depicted by FIG. 3A, the gas flow may also be generated by a pump 105 at outlet 104. This enables operation at different pressures as selected for specific species identifications.

Figure 3F:
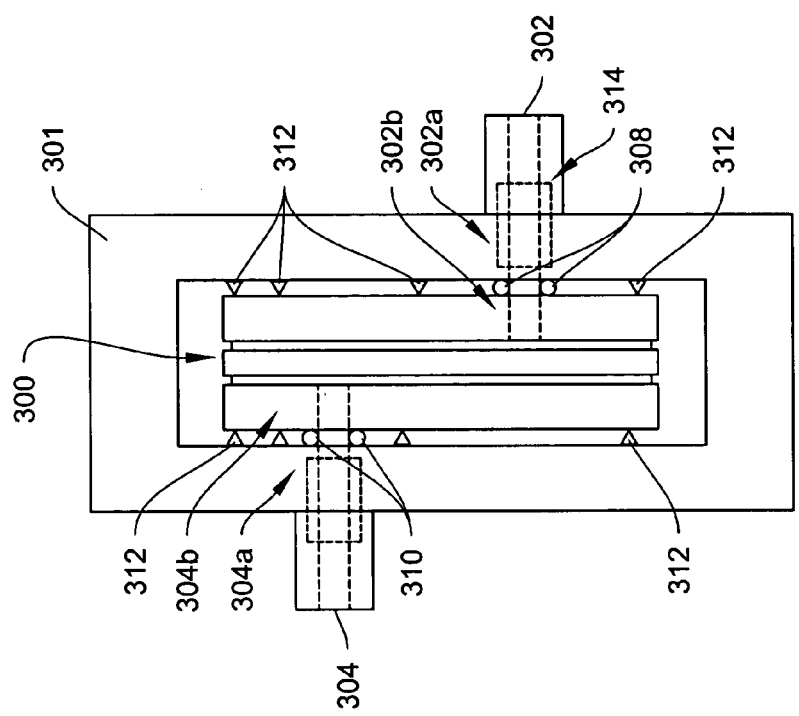
FIG. 3F is a schematic of a disposable DMS device with socket according to an illustrative embodiment of the invention.

It is further noted that while a particular pinout is shown in FIG. 3A for mounting chip 100 in socket 106, alternative configurations are possible, all within the scope of the invention. For example, as shown in FIG. 3F, a DMS chip assembly 300 embodiment of the invention is mounted into a socket 301, wherein an inlet 302 on the socket provides input flow into chip 300 via ports 302a and 302b and an exhaust is provided at outlet 304 via ports 304a and 304b. In this embodiment, sealing elements 308 and 310, such as o-rings, ensure a substantially leak-free coupling of the chip 300 to the socket 301 and between cooperating ports 302a–302b and 304a–304b. An ionization source is preferably encompassed within chip 300. In one illustrative embodiment, source 314 is formed associated with inlet 302, wherein a flow of ions is supplied to the internal flow path. The chip and socket combination enable implementation of a system such as shown herein, and may be provided with connectors 312 for communication with the electronic drive and control part 40 (of, for example, FIG. 1).

Ion Control

Illustrative embodiments of the invention feature ion charge dissipative and/or controlling aspects. In one embodiment, charge dissipative parts of the flow path prevent charge buildup that otherwise can impact ion behavior. In another embodiment, electronic control of ion behavior provides optimization of mobility-based ion species filtering and control. The charge dissipative and electronic control aspects may be implemented from the same surfaces or structures or may be separately implemented.

In an illustrative practice, the invention employs a structure of partially-conducting control material supporting a plurality of control electrodes in the ion flow path. These supported control electrodes are laid out as an addressable array (which may be a grid of electrodes). Controlled voltages are applied to such addressable array to affect and control local ion behavior in the flow path. This control function of the invention may be achieved using a material element or elements (in the flow path) having the capacity to conduct a charge while simultaneously maintaining sufficient electric separation between electrodes in conductive contact with that material to avoid excessive or unwanted current flows.

Such control material is generally described herein as "partially conducting," which may also include materials that are somewhat "resistive." As well, several partly- or fully-conductive elements may be gathered in an area to perform a control or a charge dissipating function.

In illustrative embodiments, the partially conducting control material may be a structure, layer, surface, covering, coating, substrate, region, or the like. In one embodiment, the control material is associated with control of an addressable array of electrodes. In one illustrative embodiment, resistive paint (used in electronic circuit applications) is applied to a non-conducting substrate with an array of electrodes formed thereon. In another illustration of such control material, a sheet of semi-conducting material is used as a partially-conducting member and as a support member (e.g., a substrate) for the array of electrodes that are used for such control function. Illustratively, the partially-conducting control material is tied to a potential or ground to dissipate the charge build-up thereat.

FIG. 4A shows DMS chip 200 in which electronic control of ion behavior is obtained. This electronic control is implemented via partially-conducting control material which forms surfaces of chip 200. In particular, flow path 201 is defined between structures 210 and 214. The structures 210 and 214 are formed as, using, or in cooperation with, partially-conducting control material layers 211 and 215, respectively, and in a one illustrative embodiment, such arrangement also provides substrate support.

Each of the partially-conducting control material layers 211 and 215 includes an electrode, or, as shown, includes an array of electrodes 211U and 215D, respectively. The arrangement of electrodes for a particular array may be chosen for particular purposes. For example, the arrays may be driven to concentrate or focus ions in the ion flow in the filter.

In one embodiment, the arrayed electrodes are used for charge dissipation. In another embodiment, they are used for ion flow control. In another embodiment, they are used for both functions. Illustrative array patterns are shown in FIGS. 4A–4D. The arrays may be formed on an insulating surface or directly on charge-dissipating surfaces in a practice of the invention.

In an illustrative embodiment, the arrays face each other and enable forming and controlling the DMS filter field F across the flow path. Such arrangement enables forming a non-uniform filter field which enables focusing or concentrating desired ion flow (such as focusing toward the center of the ion flow in the flow path). In one practice of the invention, at least one array is employed, which faces at least one electrode but preferably faces an opposed array of electrodes on opposed sides of flow path 201, and which are driven to create the non-uniform field to achieve such concentrating effect. It should be noted that a uniform field would not achieve such ion focusing.

Referring to the illustrative embodiment of FIG. 4A, arrays 211U and 215D, are formed on partially-conducting control material layer 211 and 215, respectively. These arrays include a plurality of electrodes, such as electrodes 211a–211n of array 211U and electrodes 215a–215n of array 215D, in the pattern shown in FIG. 4B. For ease of illustration, layer 211 is treated as if transparent, wherein it will be understood that electrodes 211a–211n forming array 211U are, in fact, on the inner face of layer 211. Also included are leads 211a1–211nl for communication therewith. A like configuration is applied to layer 215 with electrodes 215a–215n of array 215U and leads 215a1–215nl. The arrays face each other across flow path 201.

Figure 4E:
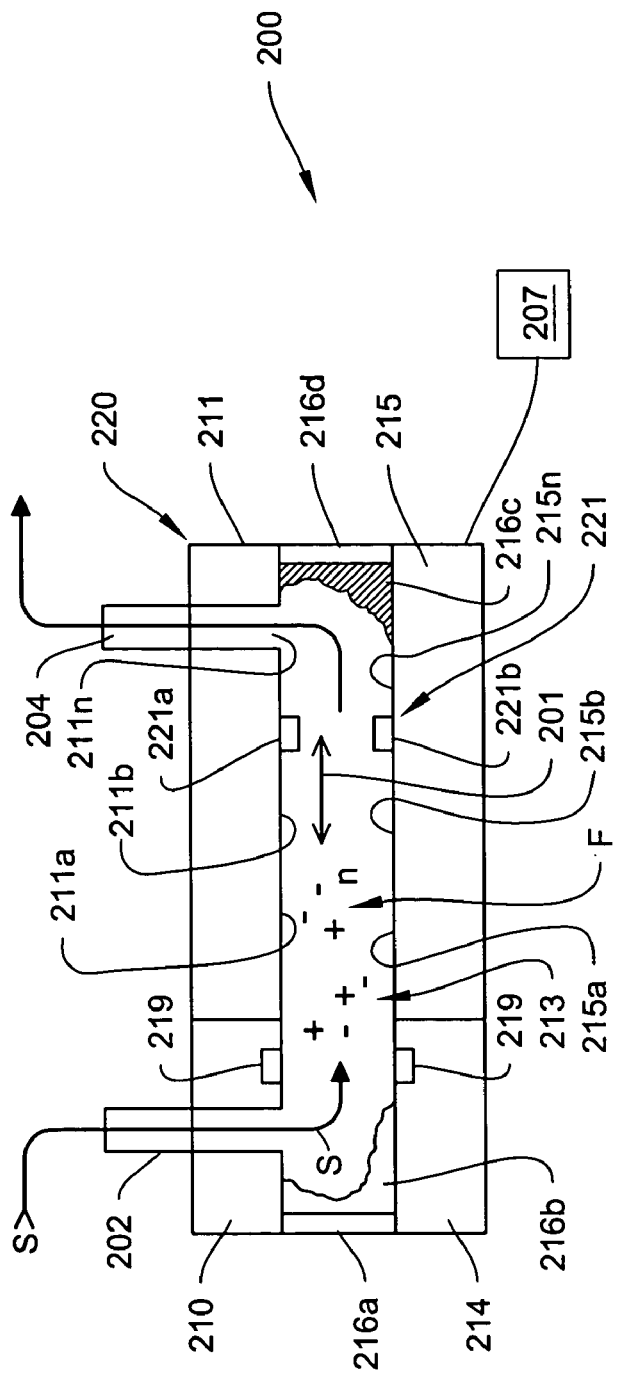
FIG. 4E is a side view of a DMS system according to an illustrative embodiment of the invention.

As shown in FIG. 4E, structures 210 and 214 act as support members (e.g., like substrates) and cooperate with spacing sidewalls 216a–216d, to form a housing or package 220 for DMS chip 200. Sidewalls 216b and 216c are shown in partial view for clarity. These sidewalls may be formed in various manners and may form all or several sides of the chip. For example, sidewalls 216 may be discrete such as by using a spacer frame 112, as earlier set forth, or may be formed as extensions of the structures 210 and 214, as shown in FIG. 4E.

Sidewalls 216a–216d may be used as confining electrodes or for charge dissipation, and may include conducting or partially-conducting surfaces. These sidewalls may be tied to a potential or to ground or may be driven as per the other electrodes of the invention.

In one illustrative embodiment, the sidewalls are defined by spacer frame 112 (FIG. 3D) which is formed of a dielectric material. In one illustration, a negative potential is applied to the spacer frame such that the sidewalls act as concentrating electrodes to concentrate ions toward the center of the flow path, which intensifies the analyte for downstream analysis.

Returning to FIG. 4E, the I/O function of chip 200 includes an inlet tube 202 for receipt of a gas sample from the environment (or from a GC outlet or the like), and an outlet tube 204 which may be coupled to a pump (not shown) for exhaust of air flow and/or delivery of filtered ions for further downstream processing. An ionization source 219 may also be provided which may include UV, Ni63, ESI, corona discharge, atmospheric pressure chemical ionization (APCI), matrix-assisted laser desorption ionization (MALDI), plasma, or the like.

As shown in FIG. 4E, the chip 200 includes ion filter 213, which functions similarly to filter 108F of chip 100, and preferably also includes a detector 221, similar in function to detector 108D of chip 100. Electronic ion control is provided by a controller 207, similar to controller 107 associated with chip 100 (FIG. 3A), or controller 40 associated with apparatus 10 (FIG. 1). The system is controlled and ion detection signals are evaluated and reported by the controller 207. Chip 200 has electrical connectors, such as leads 211a1–211nl and 215a1–215nl, enabling connection to the controller 207, whether it is situated on or off-board of chip 200.

In operation, sample S is drawn in through inlet 202 and flows along flow path 201. If the sample flow is not yet ionized then it is being subjected to ionization source 219. In any event, ions ++,−−, and n flow along the flow path toward outlet 204 and into filter 213. Electrodes 211a–211n, and 215a–215n, of the respective control arrays 211U, 215D are addressed, and controlled DMS voltages are applied to such electrodes, to create a compensated RF field F to affect ion behavior in ion filter 213. Ion species of interest are thus passed through filter 213. Illustratively, the passed ions are detected at on-board detector electrodes 221a and 221b of detector 221 (FIG. 4E), which function in the manner discussed above with respect to DMS system embodiments 10 (FIG. 1) and 100 (FIG. 3A).

Figure 5A:
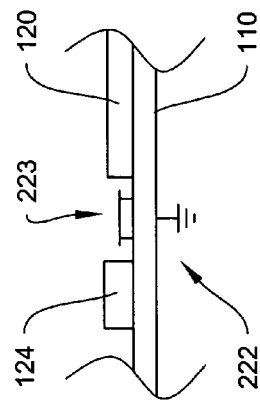
FIGS. 5A–5C show alternative charge dissipation embodiments of the invention.
Figure 5B:
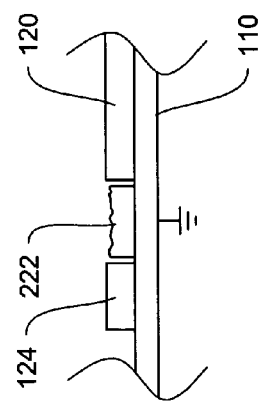

FIGS. 5A–5B show several further illustrative charge dissipating applications of the invention, implemented on substrate 110. Spacer 112 and the other substrate 114 are not shown, but may also be adapted accordingly.

As shown in FIG. 5A, filter electrode 120 and shielding electrode 124 are located on substrate 110 separated by a charge dissipation layer 222. In FIG. 5B, a charge dissipating electrode (or collection or array of electrodes) 223 performs the charge dissipating function of the invention between electrodes 120 and 124. In these embodiments, charge dissipation reduces, or in some instances minimizes, charge buildup and facilitates an improved ion analysis by conducting charge away from the ion flow and from the analytical region of the flow path.

Figure 5C:
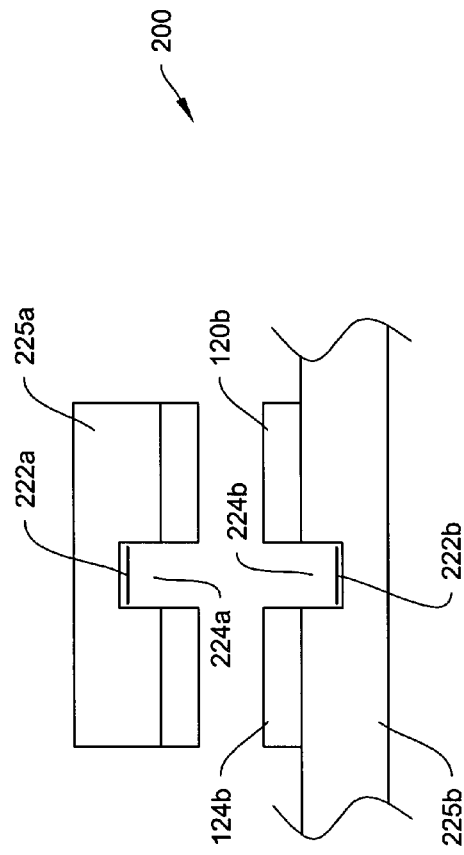

In FIG. 5C, an ion-based analytical system 200 includes cooperating substrates 225a and 225b. Relief from charge buildup is provided by recesses 224a and 224b located where the charge might otherwise build and interfere with the ion flow. More particularly, and referring to substrate 225b (it being understood that cooperating substrate 225a is similar and therefore is not shown in detail), it will be seen that recess 224b is formed to effectively relocate the area where charge buildup might otherwise occur along the flow path between electrodes 120b and 124b. The effect is to lessen or prevent unwanted charge buildup from interfering with local ion flow. The result is improved stability of ion-based analytical system 200.

Optionally a charge dissipating layer 222b also is formed at the bottom and/or sides of recess 224b to further ensure reduction, or in some instances minimization, of charge buildup. The result is improved stability of ion-based analytical system 200.

Figure 5D:
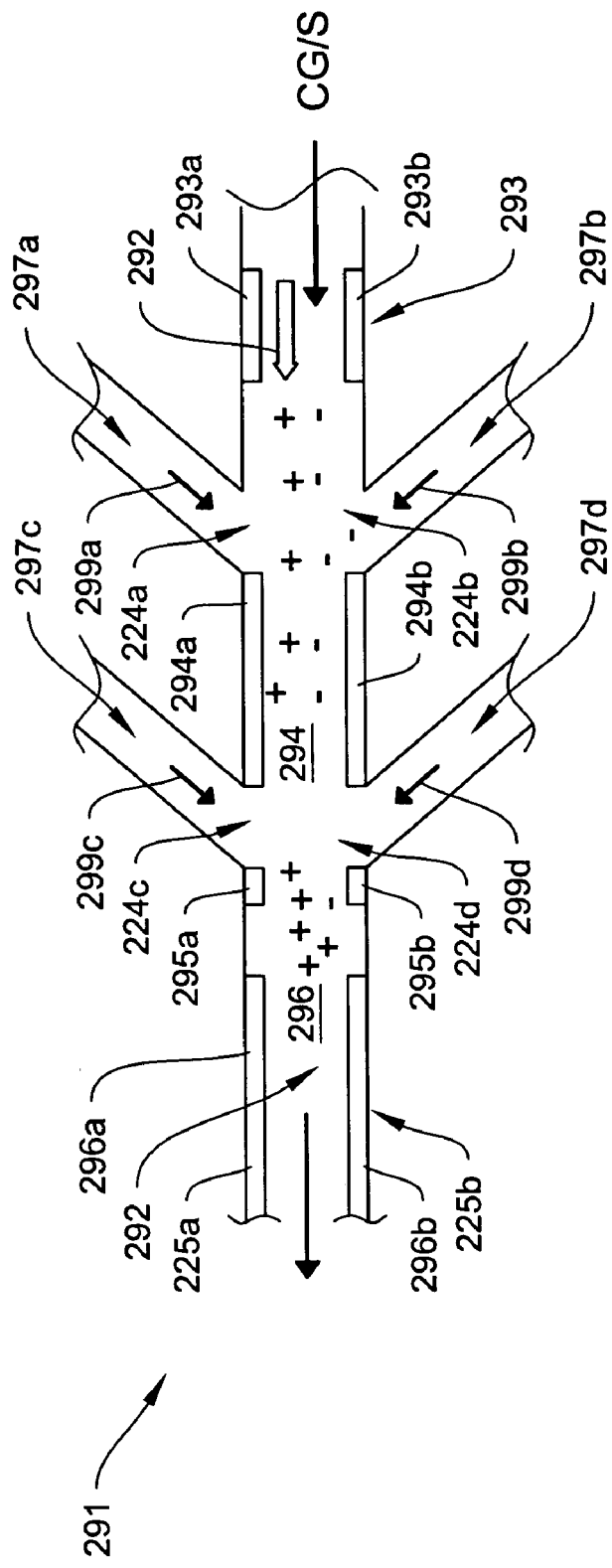
FIG. 5D shows a system having multiple flow paths that reduce charge build-up and enable ion concentration according to an illustrative embodiment of the invention.

In FIG. 5C, the effects of charge buildup are reduced by recessing the charge building surfaces away from local electrodes, such as achieved with recesses 224a and 224b. A variation is shown in FIG. 5D, wherein recesses 224a–224d are provided to reduce, or in some instances minimize, the likelihood of charge buildup interfering with the analytical flow. FIG. 5D illustrates a multi-flow path embodiment of the invention which reduces charge buildup and also enables ion concentration.

More specifically, analytical device 291 receives a flow, such as a carrier gas CG with sample S, into flow path 292 and into ionizer 293, the latter illustrated having electrodes 293a and 293b. Ions ++,−− are generated and flow into DMS ion filter 294 between filter electrodes 294a and 294b. A selected ion species ++ is passed through filter 294 according to the filter field, flowing past guard electrodes 295a and 295b and into detector 296 to be detected by a detector electrode 296a or 296b, according to polarity.

Recesses 224a–224d are respectively defined by the mouth of a respective flow path 297a–297d joining flow path 292. Flow paths 297a–297d permit a gas inflow or outflow. In a further embodiment, the respective flow paths 297a–297d enable introduction of containment gas flows 299a–299d. For example, flow 299d from path 297d flows into flow path 292. The flow 299d joins the ion flow ++,−− at an angle which enables the flow 299d to drive the ion flow ++,−− toward the center of flow path 292. Preferably flow 299d cooperates with containment flows 299a–299c to achieve ion concentration toward the center of flow path 292. Thus, in addition to controlling charge build-up, in this embodiment, an ion-concentrating function is provided to concentrate the ion flow and to further improve system performance.

Electrospray and Charge Dissipation

DMS systems work favorably with, and can benefit from control of, charged surfaces along the flow path. In one illustrative embodiment, a charge field is established along the flow path. In another illustrative embodiment, filter and detector electrodes are isolated from each other to prevent interfering with ion detection. This separation can be achieved by insulating the electrodes, such as by building on insulated substrates.

At times, it may be required to reduce charge buildup on the flow path surfaces (e.g., at least a portion of the surface $110a$ of substrate 110 of FIG. 3B). The invention provides the option of charge dissipation without interfering with action of the filter and detector electrodes. In one exemplary embodiment, electrospray ionization in DMS is employed while reducing the effect of surface charge buildup on the exposed surfaces of the flow path, which includes exposed surfaces in between the electrodes. The charge-dissipative (e.g., partially conducting) control material of the invention forms a charge dissipation path to reduce charge buildup. The ionized electrospray flows through the DMS filter with regularity. Thus, the control material of the invention is used to form a charge-dissipative surface to replace or augment or cover or cooperate with the filter electrodes and the other surfaces of the flow path.

Figure 6A:
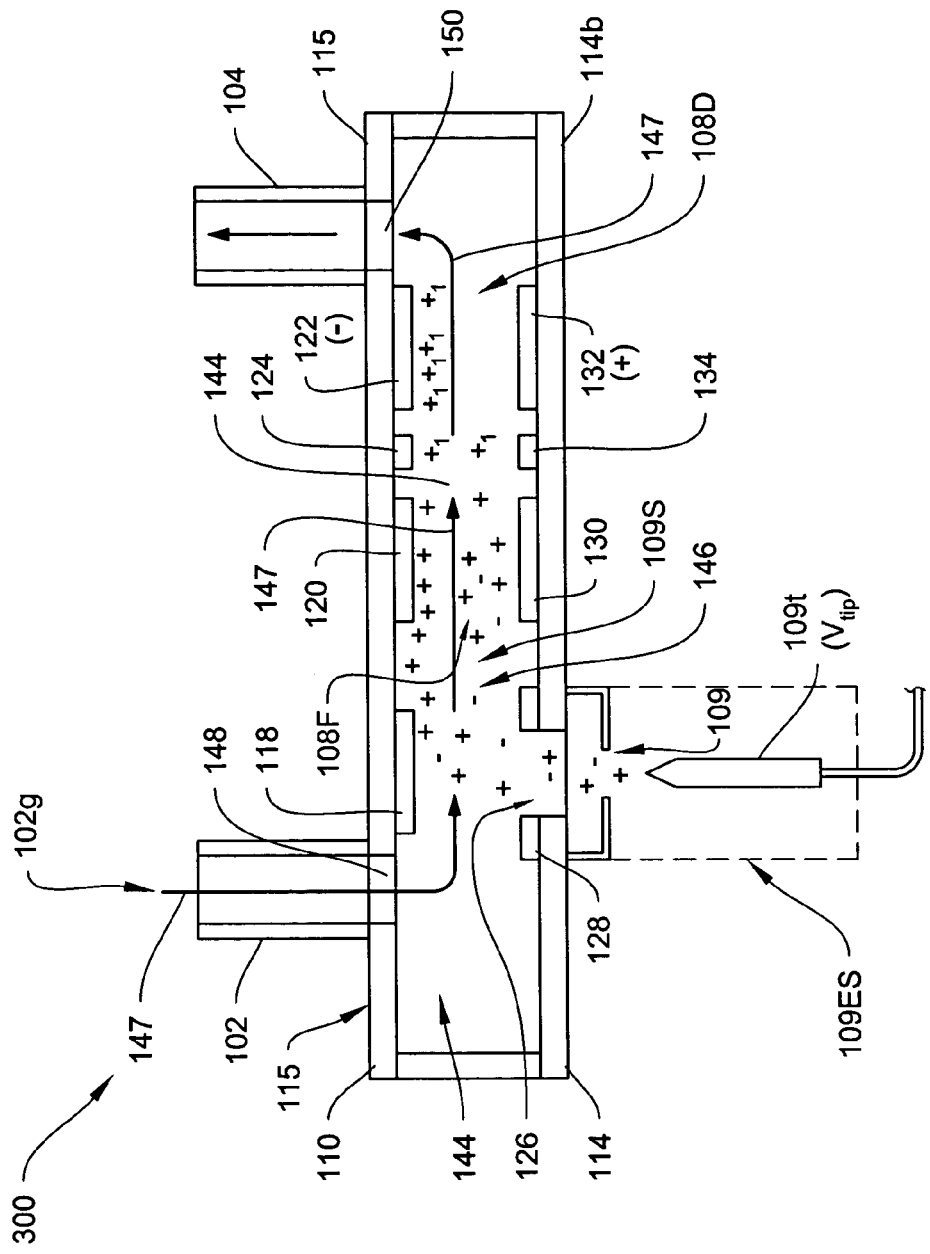
FIG. 6A shows a side schematic view of an alternative DMS chip according to an illustrative embodiment of the invention.

The embodiment of FIG. 3E can be modified according to the invention, as shown in FIG. 6A, to utilize an electrospray head 109ES attached to chip 300, such as at substrate 114. In an ESI-filter assembly 300, carrier gas $102g$ is introduced via inlet 102 and the sample to be filtered is ionized and introduced via the electrospray head 109ES as ionized sample stream $109s$. The electrospray tip $109t$ is held at a high electrical potential (Vtip) and charges the atomized ionized spray molecules (positive or negative, but shown as +,+,+), which are attracted by oppositely-charged attractor electrode 118 as they flow through ionization access port 126 into flow path 144. The ionized sample $109s$ is conveyed along the flow path and into in the analytical gap between filter electrodes 120 and 130 of ion filter 108F.

In this illustration, these ions (+,+,+) are subjected to the compensated asymmetric RF field of filter 108F. The species of ions that are returned toward the center of the flow by practice of embodiments of the invention will pass as species $+_1$ into the detector. If these are positively-charged ions, then a positive bias on detector electrode 132 steers the ions toward negatively-biased detector electrode 122 with which these positive ions make contact and where they deposit their charges. (Negatively charged ions can be detected in a similar manner, with opposite polarity biasing.)

The ion species detection and the intensity of detection are correlated with the parameters of the filter environment, which is evaluated against a library of information for identifying detected species. Finally, the ions $+_1$ having lost their charges return to being neutral molecules and they and the rest of the gas flow are carried out of the detector region via outlet 104.

Figure 6B:
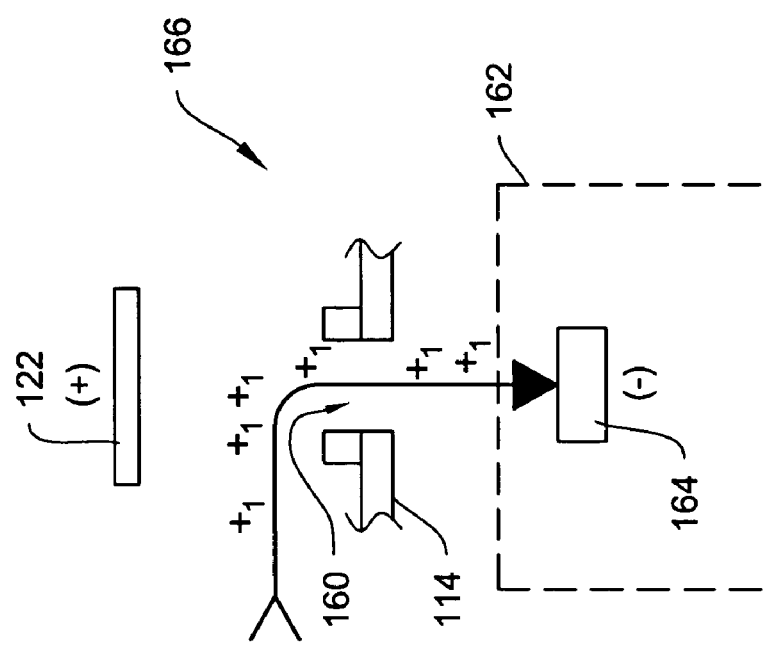
FIG. 6B shows an alternative detector arrangement according to an illustrative embodiment of the invention.

FIG. 6B shows an alternative arrangement, where the separated ions $+_1$, $+_1$, $+_1$ are outputted for external use. In such embodiment, detector electrode 122 is opposite an orifice 160 in substrate 114 and the biased electrode 122 (e.g., positively biased) steers ions $+_1$, $+_1$, $+_1$ toward the orifice where they flow out of the flow channel. In one embodiment, this enables the ions to be delivered to the input of a mass spectrometer 162, which may be assisted by an attraction electrode 164 (in this example negatively biased to attract ions $+_1$, $+_1$, $+_1$). This arrangement may further include an electrode ring 166 which cooperates with orifice 160 for the passage of ions $+_1$, $+_1$, $+_1$ out of the flow channel, while also being capable of being biased to attract a portion of the ion flow $+_1$, $+_1$, $+_1$. Now, feedback and control data may be obtained at electrode ring 166 as a detector, for the operation of the filter system of the invention, while also enabling a desired ion output.

As can be seen from the above discussion, an electrospray head provides a highly ionized sample flow into the flow path. In some illustrative embodiments, the invention combines an electrospray with previously discussed partially-conductive aspects, such as the earlier described partially-conductive layers 211 and 215. These charge-dissipative surfaces carry away the "static" charge build-up and further enable ion analysis in an electrospray-DMS system of the invention.

Control of Ion Motion

In several illustrative embodiments of the invention, controlled voltages are applied to control surfaces and/or control electrodes (which may be formed as arrays) to affect and control local ion behavior, density, or concentration. This may also include control or influencing of ion velocity and/or direction of ion travel, even by species.

Illustratively, in the device 200 of FIG. 4A which includes electrode arrays 211U and 215D facing each other over the flow path 201 and ions flowing through the analytical gap G in between these arrays, several aspects of species-specific ion motion control may be implemented. The ion motion control may include, for example, application of a longitudinal propulsion field for propulsion of ions along the flow path, generation of the DMS RF filter field to affect differential transverse ion motion in the filter, and/or compensation of the DMS filter field to select ion species for passing through the filter field.

Generation of the DMS RF filter field and compensation of the field have been set forth in U.S. Pat. No. 6,459,823, incorporated herein by reference. Electric field propulsion of ions along a DMS flow path has been set forth in U.S. Pat. No. 6,512,224, also incorporated herein by reference. The electrodes in electrode arrays 211U and 215D can be driven to achieve such ion filtering, propulsion and the like.

Figure 7A:
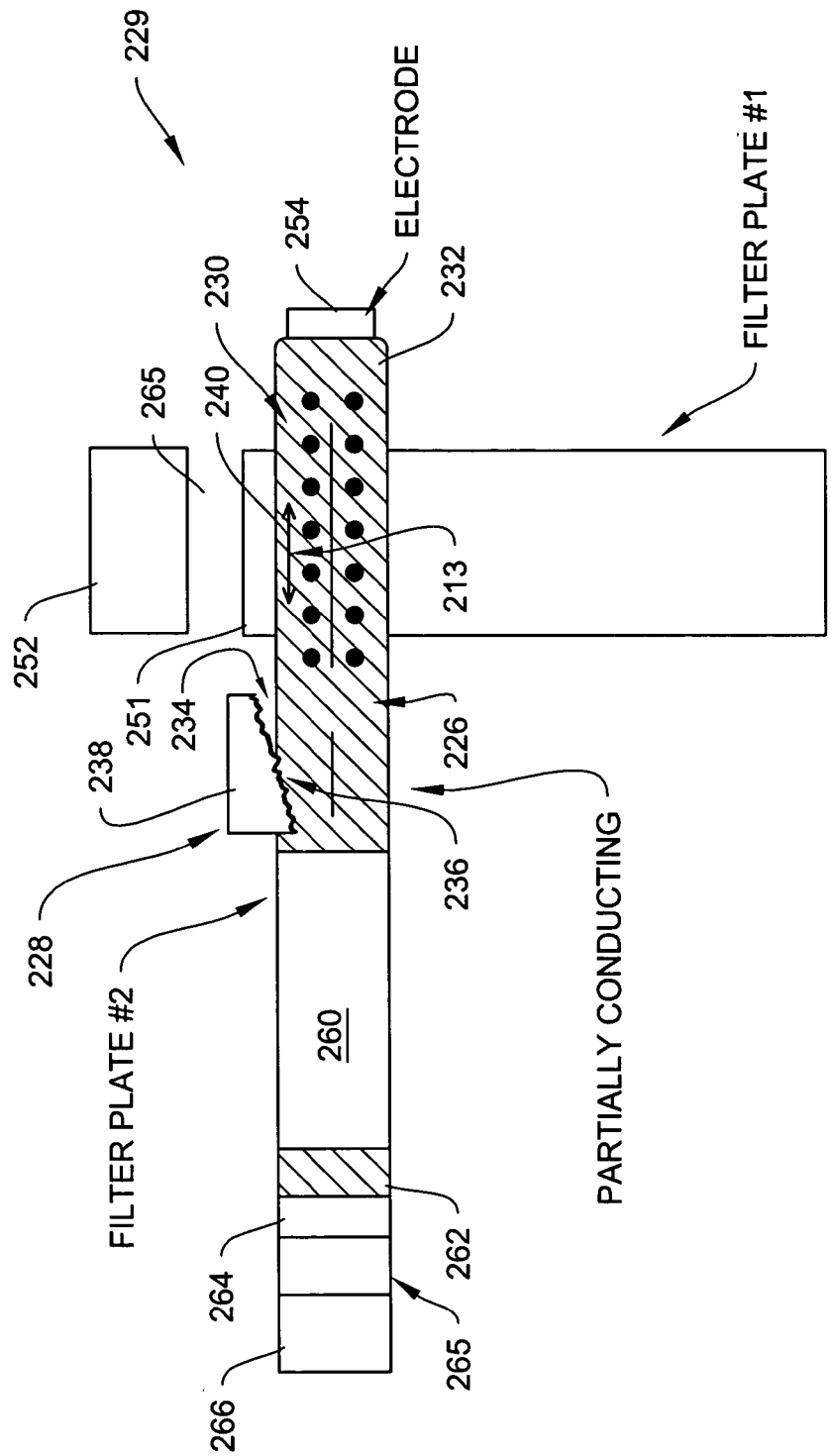
FIGS. 7A–7B are schematic views of alternative illustrative embodiments of the invention having multiple flow paths.

Electrodes or combinations of electrodes of the electrode arrays may be driven to steer, focus, confine or trap the ion flow, as well as to reduce fringing fields or to achieve other field affects. An ion steering illustration is provided in the layout of FIG. 7A, where a DMS filter 228 is formed by facing surfaces (e.g., substrates) 226 and 234 of chip assembly 229. In FIG. 7A, surface 226 and associated components are shown and surface 234 is only partially shown.

Electrode array 230 is formed on partially-conductive material layer 232 associated with surface 226; array 230 operates in cooperation with an array 236 formed on opposed partially-conductive material layer 238 on filter surface 234.

Arrays 230 and 236 are driven to perform ion control functions of the invention as applied along flow path 240. In addition, or alternatively, layers 232 and 238 can include a resistive coating over which a voltage is dropped to create a steering field for steering ions accordingly. Ions flow along flow path 240 into filter 228 and are filtered according to the variously described approaches of the invention.

In one illustrative embodiment, ion species output from an upstream filter (e.g., filter 213 of FIG. 4E) pass across flow path 240, across a guard electrode 251, to reach detector 252 for detection and identification of passed ion species.

However, in a further embodiment, a steering electrode 254 at one end of flow path 240 has a potential applied to steer and propel ions of a polarity (e.g., positive) outputted from filter 213; these ions are carried along flow path 240 so as to be subjected to arrays 230 and 236 of filter 228. The other ions (e.g., negative) are attracted toward electrode 254 and are not flowed to filter 228 at that time.

Figure 7B:
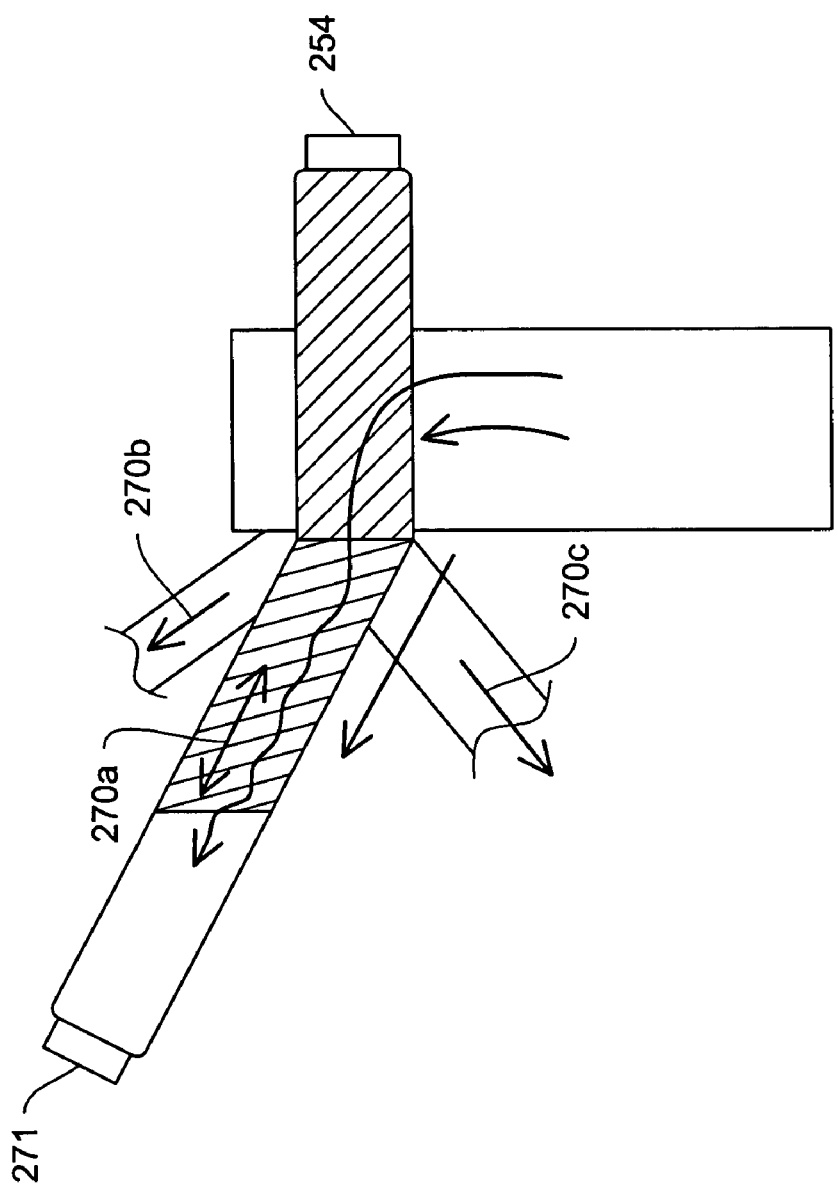

In the embodiment of FIGS. 7A–7B, arrays 230 and 236 enable performance of a number of local functions that impact the local ion flow in the flow path 240 defined between the facing substrates 226 and 234. As well, an additional filter 260 may be added to flow path 240 to enable further sample/species filtering, and it may include further partially-conductive layers 262 to control charge buildup.

A detector electrode 266 can be provided that detects the passed ions. The guard electrode 264 is isolated (such as by insulated land 265) from the detector electrode 266 so as to prevent filter signals from interfering with the detection signal. A similar arrangement is applied to guard electrode 251.

In a further embodiment of the invention, as shown in FIG. 7B, ions that arrive from filter 213 and are steered by electrode 254 may obtain an angular vector that can be anticipated and accommodated by having one or several angled filter path(s) 270a–270c. Appropriately deflected ions flow along flow paths 270a–270c for further processing. Additional collection or attraction electrodes, e.g., electrode 271, may also be provided to further assist ion separation and/or analysis. Thus, ion species having a first characteristic may be deflected into path 270a, while ion species having a second characteristic may be deflected into path 270b, and yet another into path 270c, which may reflect ion mobility, weight, mass, or other characteristics.

Figure 8B:
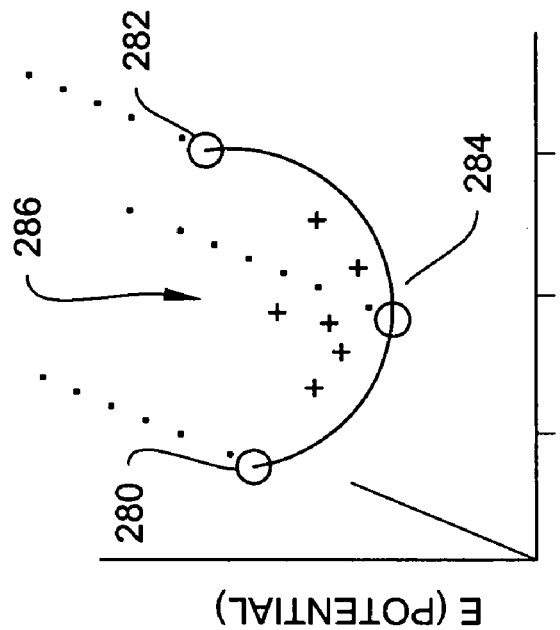
Figure 8A:
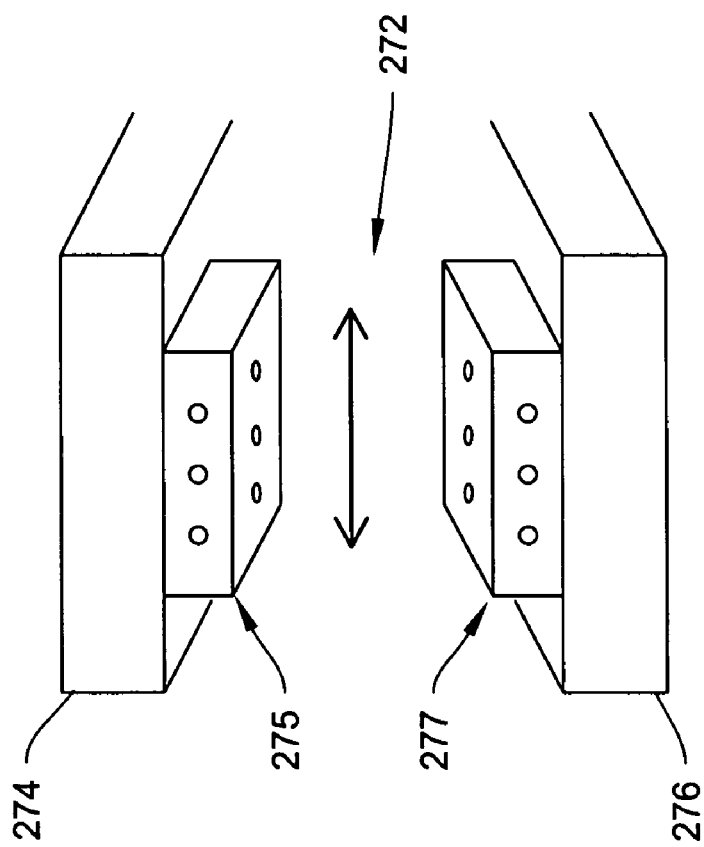

FIG. 8A shows a filter 272 having upper and lower electrode arrays 275 and 277 formed on partially-conductive material layers 274 and 276, respectively, according to another illustrative embodiment of the invention. By appropriately driving various ones of these electrodes, ions of a given polarity can be steered or collected at various locations within the flow path.

Ion control is further described with respect to FIG. 8B, where the effect of having different potentials (varied over time) applied to parallel electrode columns 280, 282 and 284 is to create a potential "well" or "trough" 286 in which ions of a given mobility aspect can collect, producing a condensing or focusing effect. This can be explained with respect to polarity, for example, where electrodes 280 and 284 are positive and electrode 282 is less positive, and therefore positive ions (ions +,+,+,+ in FIG. 8B) tend to collect in the trough 286.

Figures 9A, 9B:
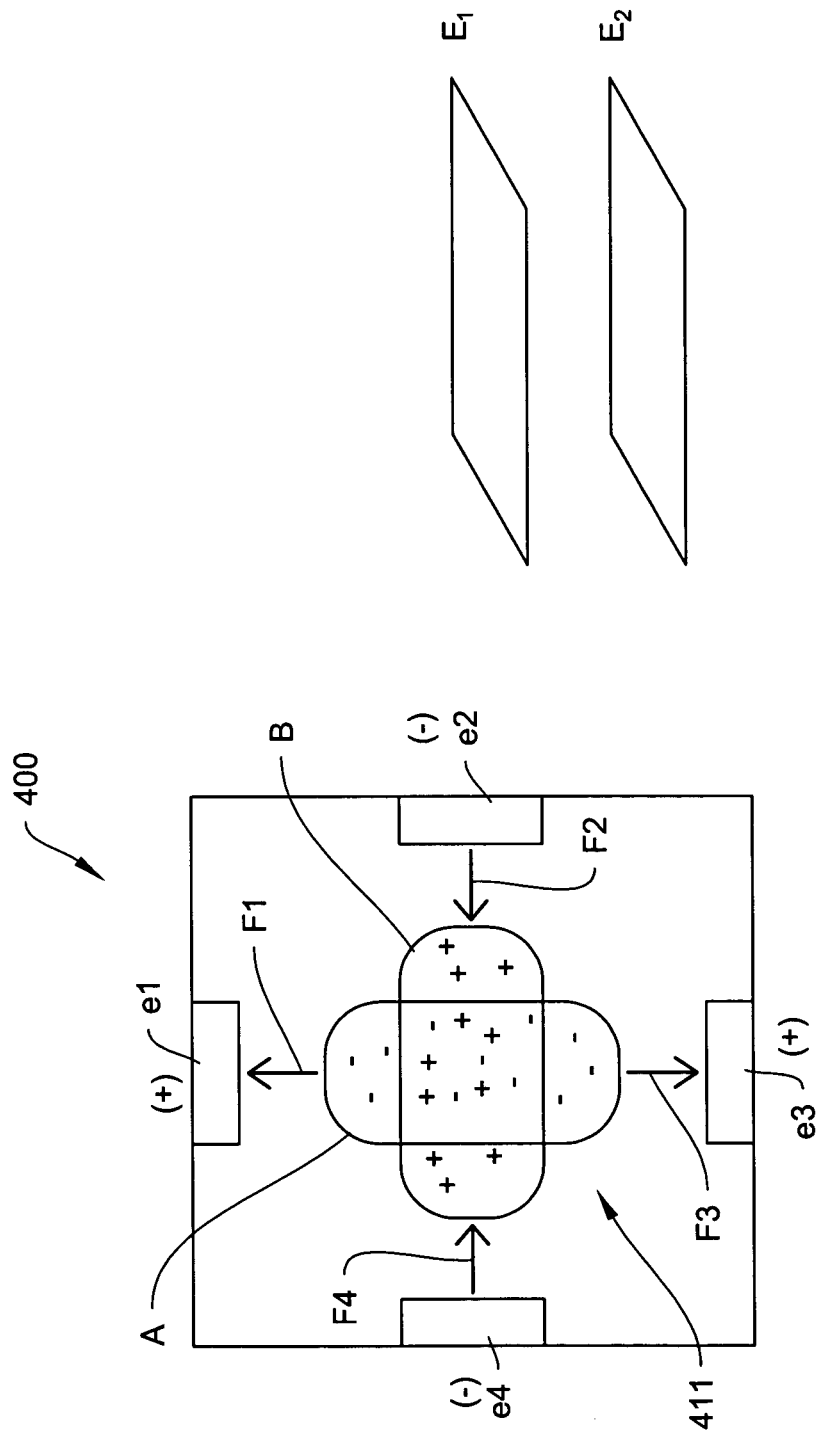

FIG. 9A shows a plurality of ions ++,−− near the center of flow path 411 in an ion-controlling embodiment 400 of the invention. In an illustrative embodiment, electrodes e1 and e3 are biased positively with respect to electrodes e2 and e4. The negative ions typically tend to concentrate as shown in or about cloud A, whereas the positive ions typically tend to concentrate in or about cloud B. The field in the vicinity of each electrode is shown as F1–F4, respectively. These ions are thus segregated and concentrated by action of fields F1–F4 between cooperating concentrator electrodes e1–e4. The concentration field generated between these electrodes concentrates the ions toward the center of the flow path, which may be implemented before, during or after ion filtering.

In a preferred embodiment, the concentrator electrodes are driven sequentially. This phased drive is shown in FIGS. 9B–9E, where impulses $E_A$, $E_B$, $E_C$, and $E_D$ are sequentially applied to respective electrodes e1–e4, by a phased application of asymmetric waveform 402. This is shown in a two-electrode arrangement (FIG. 9B), four-electrode arrangement (FIG. 9C), and alternatively in a three-electrode arrangement (FIG. 9E), but may also be achieved with other numbers of electrodes.

Figure 9G:
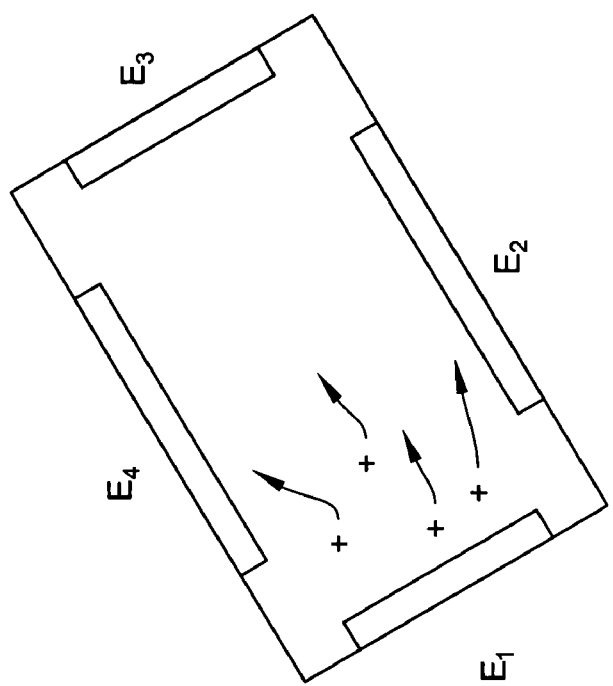
FIGS. 9G–9J show concentrator electrodes and drive signals according to various illustrative embodiments of the invention.
Figure 9F:
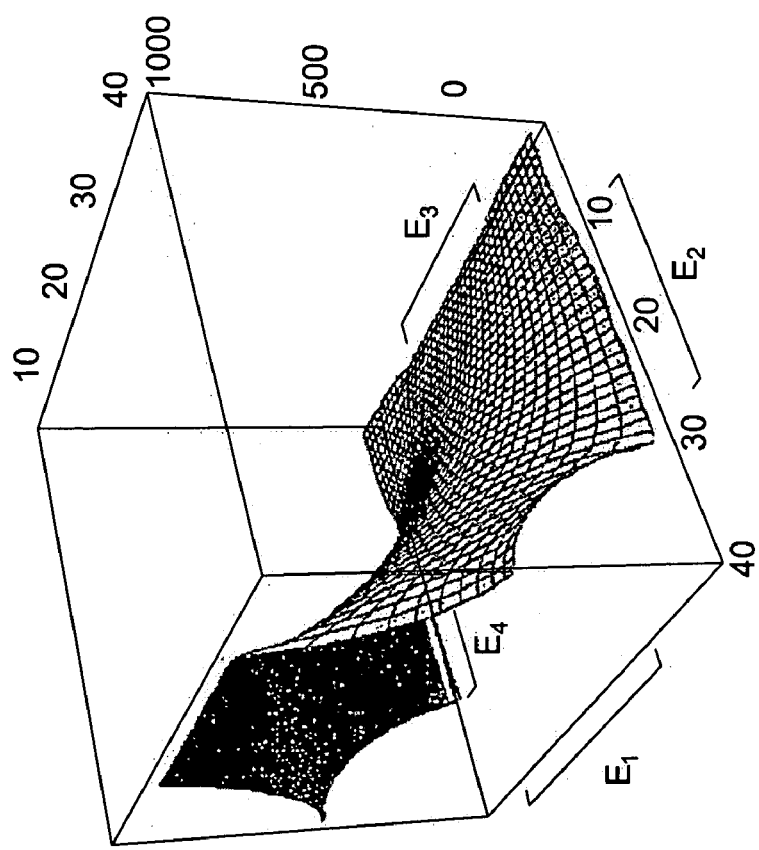
FIG. 9F shows a concentration profile according to an illustrative embodiment of the invention.

The forces in one phase can also be visualized as gradients on a potential energy surface, such as shown in FIG. 9F. In this embodiment, the net effect over all four phases, i.e., one for each electrode, is to concentrate certain ion species into the center of the flow path according to species characteristics. This typically enables ion species separation.

Thus a positive impulse from phased application of drive waveform 402 will drive ion species responsive to that waveform and impulse to be either concentrated or deconcentrated according to their DMS behavioral characteristics. Each waveform will affect various ion species differently. Thus, drive waveform 402 can be selected according to known ion species behaviors to facilitate the analytical process.

As further shown in FIG. 9G, four electrodes are used to generate an inhomogeneous electric field in the space between them (i.e., typically transverse to the ion flow path). In each of the four phases a different voltage is placed on one plate, thus having a different plate in each phase. The net effect on the ions can be a motion towards the center of the channel and away from each electrode. The net forces on some ions in the vicinity of E1 is shown.

Therefore, substantial ion flow control can be imposed in practice of embodiments of the invention. The concentrated ions flow downstream for filtering and detection with improved resolution and better sensitivity. In one illustration, ions are concentrated between arrays of electrodes, and then are filtered downstream. Ion detection is then correlated with the drive signals applied to the array and ion filter, and ion species identification is made, by, for example, referring to a lookup table of stored ion behavior.

Figure 9H:
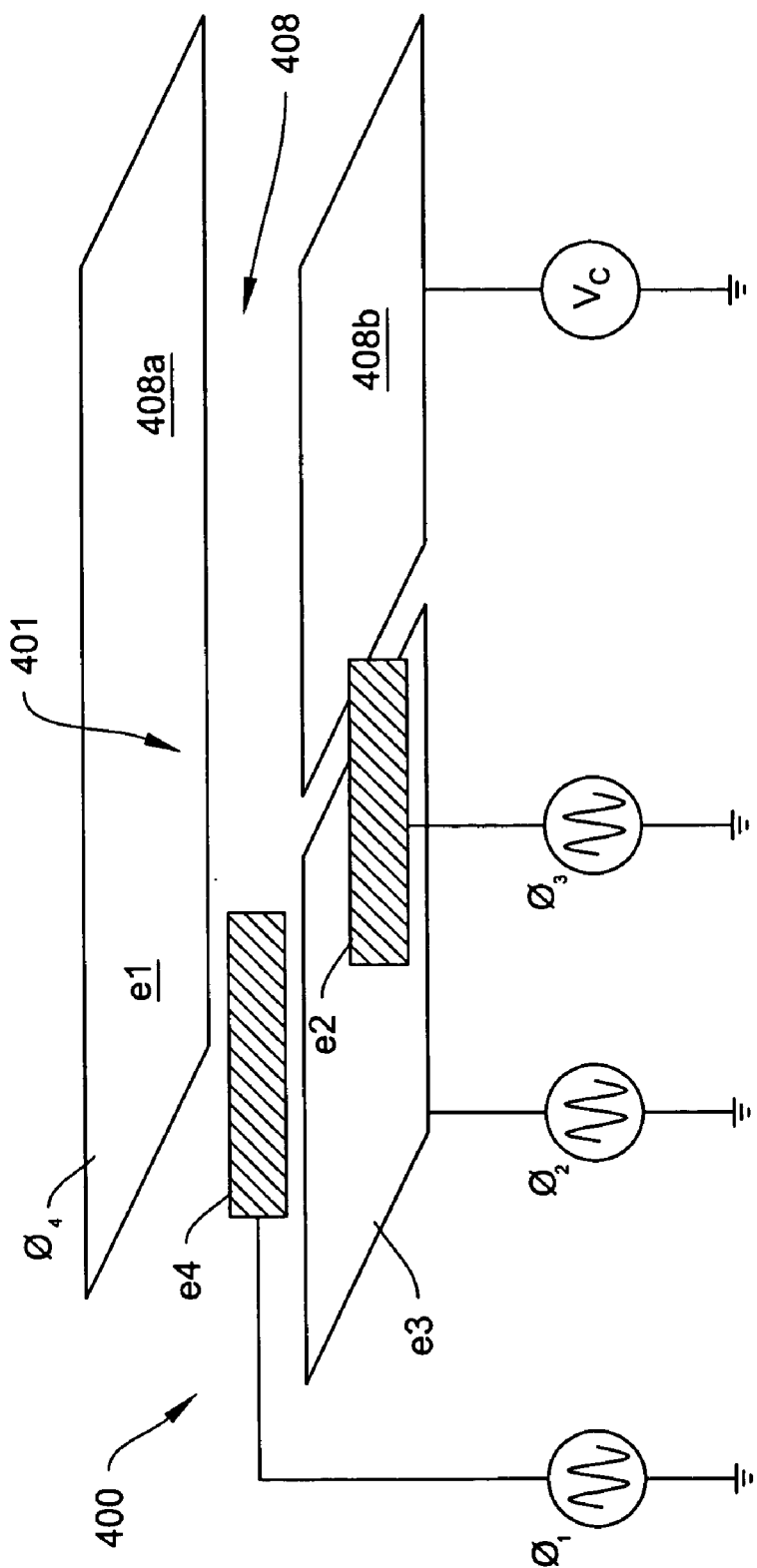

To concentrate ions toward the flow path center, the concentrator electrodes need not be entirely separate from the filter electrodes. As shown in the illustrative embodiment of FIG. 9H, for example, concentrator 401 has concentrator electrodes e1–e4. Adjacent filter 408 has filter electrodes 408a and 408b. One filter electrode 408a is shared as electrode e1 of concentrator 401. Various of these electrodes can be driven as needed, and may be biased DC, grounded, or driven with RF, consistent with the teachings of the invention.

Figures 9I, 9J:
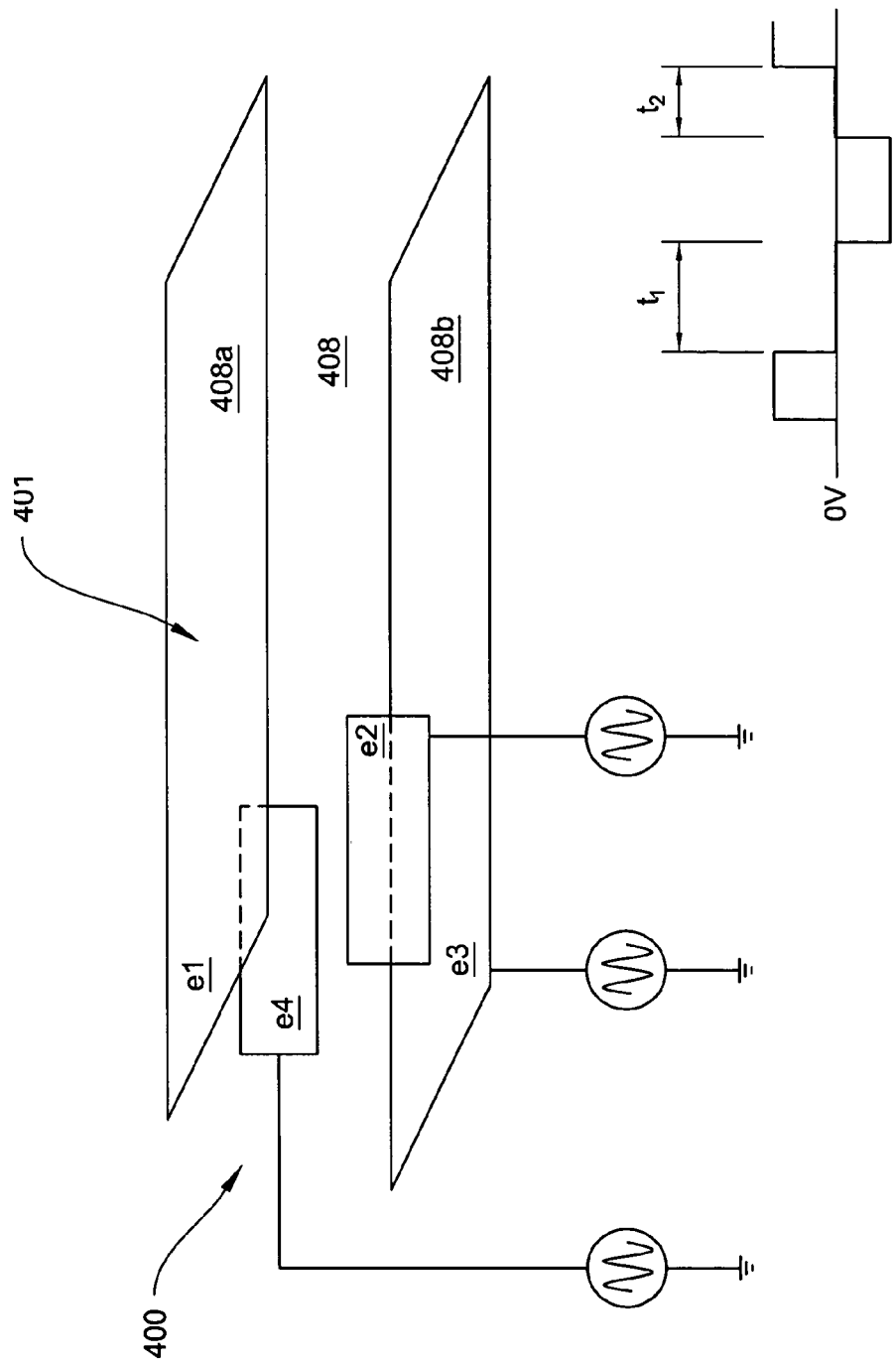

In the illustrative embodiment of FIG. 9I, the two filter electrodes are shared by concentrator 400, i.e., concentrator electrodes e1 and e3 also serve as filter electrodes 408a and 408b. However, in the latter case, the drive waveform has a pause in the filter signal so that the concentrator signal may be applied. This is shown schematically in FIG. 9J, where waveform 404 is provided with a timeout at $t_1$ and/or $t_2$, in the filter signal. For example, signal $E_A$ can be applied during time period $t_1$, and signal $E_B$ can be applied during time period $t_2$, signal $E_C$ can be applied during the next period $t_1$ and signal $E_D$ can be applied during the next time period $t_2$. This illustrative embodiment enables a simplified electrode arrangement to achieve the concentration effect of the invention.

The above embodiments facilitate concentration of selected ions or concentration of ions to the center of the flow path. One objective is to enhance ion species separation and resolution in analyzing the ions.

Facing electrodes of different sizes typically generate a non-uniform field, which can be practiced in an alternative embodiment of the invention for focusing the ion flow. As shown in FIGS. 8C–8D, a non-uniform field can be generated by driving a different number of the facing electrodes in opposed electrode arrays 275 and 277. For example, electrode $E_5$ of the plurality of electrodes $E_1$–$E_n$ is driven in array 277 and cooperates with a plurality of driven electrodes $E_1$–$E_n$ in array 275. The field F generated between these electrodes is concentrated at the single electrode $E_5$ of array 277, while it is distributed between electrodes $E_1$–$E_n$ (and therefore is at lower field strength) along the face of array 275. This creates a desired condensing or focusing of ions that typically tends to improve system sensitivity.

A result of the non-uniform field is to have the desired focusing effect for collecting or concentrating of ions to assist ion analysis and detection. This on-demand or switchable or controllable ion control feature is useful, since a particular effect (such as ion focusing) has a different impact on different ion species, and therefore may be selectively used to augment species separation. According to further illustrative embodiments of the invention, the foregoing ion control is employed, for example, for texturing, controlling, manipulating, trapping and steering ion flow in the filter field for achieving desired ion behavior.

Reduction of Fringing Fields

The invention may also be applied to reducing the fringing field at the edges of the filter electrodes. In one aspect, the charge dissipation quality of the partially-conducting control material layers of the invention reduces fringing fields. In another aspect, the impact of fringing effects at the edges of the filter electrodes are reduced by appropriately driving electrodes of arrays 211U and 215D to anticipate the fringing effects and to adjust ion behavior.

The DMS filter field generated between the faces of the filter electrodes, such as filter electrodes 20 and 22 of FIG. 1 or electrodes 120 and 130 of FIG. 3E, typically are straight, uniform, and well-defined. A similar result can be achieved between the faces of electrode arrays 211U and 215D of FIG. 4A.

Figure 10A:
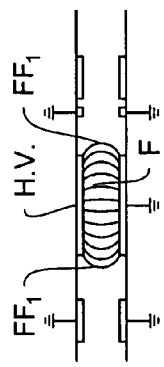
FIGS. 10A–10B show before and after effects on fringing fields according to an illustrative embodiment of the invention.
Figure 10B:
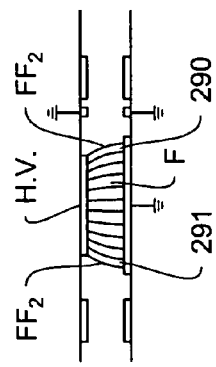

However, the fringing field around the electrode edges can be irregular and can negatively impact ion flow. As shown in FIG. 10A, the fringing field FF1 at the edges of the filter field F has a non-linear shape, which impacts the local ion flow. Nevertheless, formation of the filter arrays 211U and 215D on the partially-conducting control material layers 211 and 215 enables sculpting the fringing field effects. Therefore, as shown in FIG. 10B, in an illustrative embodiment of the invention, the fringing field FF2 that impinges on partially-conducting control material layers 290 and 291, is reduced. The result is to substantially straighten the filter field at its margins. While there still may be a vector associated with the fringing field, it is more uniform and will have more predictable local impact on ion behavior. In a further illustrative embodiment, this remaining vector is neutralized by selectively driving selected electrodes of the array of electrodes.

Figure 11:
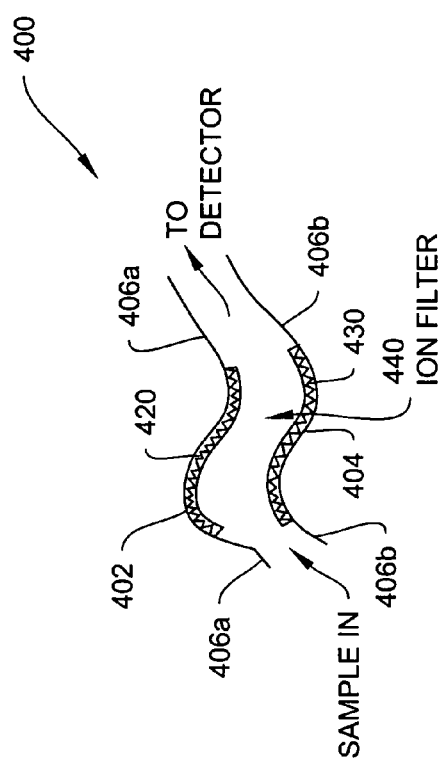
FIG. 11 shows an illustrative embodiment of the invention including a varying flow path.

In the illustrative embodiment of FIG. 11, a non-flat flow path is shown having electrodes 420 and 430 of ion filter 410. The electrodes are formed on substrates 402 and 404. Also provided are charge dissipating surfaces 406a and 406b in an illustrative embodiment of the invention.

It should be noted that that the terms spectrometer, apparatus, assembly and system may include and refer to a filter, detector, sensor, separator, and the like, interchangeably for purposes within the spirit and scope of the invention. The terms drift tube, flow path, and flow channel may be used interchangeably and remain within the spirit and scope of the invention. The terms upper, lower, inner, and outer are relative, and are used by way of illustration and not by way of limitation. Additionally, the invention is operable with gas and liquid samples, even though for convenience the illustrative examples above refer to samples in a gas flow. Further, the invention may be employed with planar, cylindrical, radial and other device configurations.

While this invention has been particularly shown and described with references to illustrative embodiments thereof, various changes in form and details may be made, without departing from the scope of the invention encompassed by the appended claims.

What is claimed is:

1. A system for controlling ion behavior for ion-based chemical analysis, said system comprising:
   a flow path for a flow of ions, an ion source coupled to said flow path, an ion filter including electrodes separated by an analytical gap for generating an ion filter field in said flow path for filtering said flow of ions in said flow path, and
   a control structure for controlling ion behavior in said flow path, wherein ions are separated according to species, said separation reflecting ion-mobility-based behavior of said ions in said filter field, wherein said control structure is at least partially conducting, having at least some capacity to conduct a charge.

2. The system of claim 1, wherein said control structure is for generating an influencing field that influences said flow of ions in said device.

3. The system of claim 1, wherein said control structure governs ion flow in said flow path to control local effects that impact ion behavior in the analytical field.

4. The system of claim 1, wherein said control structure includes an influencing source that influences the analytical environment within said analyzer.

5. The system of claim 4, wherein said control structure governs ion flow activity for at least one of focusing, trapping, confining, translating, steering, selecting, filtering, detecting and redirecting ions in said flow path.

6. The system of claim 4, wherein said control structure further comprises a plurality of control electrodes forming facing control arrays, said control arrays being addressable to control motion of ions in said flow path.

7. The system of claim 1, wherein said control structure is separated from said filter.

8. The system of claim 1, wherein said control structure performs multiple control functions, including ion filtering.

9. The system of claim 1, wherein said system is a DMS system and is operated as at least one of a spectrometer, filter, detector, and separator based on ion behavior in said filter field.

10. The system of claim 1, wherein said system is operated to determine the time of flight of ions passing along said flow path.

11. The system of claim 1, wherein said control structure includes a charge-dissipating control material in said flow path, wherein said control material enables control of charge buildup in said flow path.

12. The system of claim 1, further including an active control structure for controlling field artifacts in said flow path.

13. The system of claim 12, wherein said artifacts include fringing effects at the edges of said filter electrodes.

14. The system of claim 12, wherein said control structure includes a grid array of electrodes, wherein said array is driven to selectively control ion flow in said flow path.

15. The system of claim 1, wherein said control structure includes a control array of electrodes for affecting ion behavior in said flow path.

16. The system of claim 14, wherein said array is driven to provide a non-uniform field in said flow path.

17. The system of claim 16, wherein said non-uniform field is ion-focusing in said flow path.

18. The system of claim 17 further including a spacer, wherein said filter electrodes are formed on substrates and said filter electrodes are spaced apart by said spacer for setting said analytical gap and for forming an enclosed flow path.

19. The system of claim 1, wherein said filter field is non-uniform and ion-focusing in said flow path.

20. A system for controlling ion behavior for ion-based chemical analysis, said system comprising:
   a flow path for a flow of ions, an ion source coupled to said flow path, an ion filter including electrodes separated by an analytical gap for generating an ion filter field in said flow path for filtering said flow of ions in said flow path,
   a control structure for controlling ion behavior in said flow path, wherein ions are separated according to species, said separation reflecting ion-mobility-based behavior of said ions in said filter field, and
   a spacer, wherein said filter electrodes are formed on respective substrates and said filter electrodes are spaced apart by said spacer for setting said analytical gap and for forming an enclosed flow path, said spacer being partially conducting.

21. The system of claim 20, wherein said spacer is partially conducting and insulated from said substrates.

22. A system for controlling ion behavior for ion-based chemical analysis, said system comprising:
   a flow path for a flow of ions, an ion source coupled to said flow path, an ion filter including electrodes separated by an analytical gap for generating an ion filter field in said flow path for filtering said flow of ions in said flow path,
   a control structure for controlling ion behavior in said flow path, wherein ions are separated according to species, said separation reflecting ion-mobility-based behavior of said ions in said filter field, and
   a spacer, wherein said filter electrodes are formed on respective substrates and said filter electrodes are spaced apart by said spacer for setting said analytical gap and for forming an enclosed flow path, said control structure being formed on said substrates.

23. The system of claim 1, wherein said control structure is charge dissipating.

24. The system of claim 1, wherein said control structure is charge dissipating and further including a wall structure extending along said flow path for containing said flow of ions, said control structure being recessed from said wall structure.

25. A system for controlling ion behavior for ion-based chemical analysis, said system comprising:
   a flow path for a flow of ions, an ion source coupled to said flow path, an ion filter including electrodes separated by an analytical gap for generating an ion filter field in said flow path for filtering said flow of ions in said flow path,
   a control structure for controlling ion behavior in said flow path, wherein ions are separated according to species, said separation reflecting ion-mobility-based behavior of said ions in said filter field, and
   a plurality of flow channels joining said flow path, further including a plurality of control structures, said plurality of control structures each being formed as the mouth of a respective said flow channel, wherein said plurality of control structures reduce the likelihood of charge build-up in said flow path.

26. The system of claim 1, wherein said control structure includes a plurality of separated conductive electrodes whose combined effect is to be partially conducting relative to said filter electrodes, wherein said plurality is isolated from said filter electrodes for dissipating charge build-up in said flow path.

27. The system of claim 1, wherein said control structure includes partially conducting material selected from the group consisting of: semiconductor material and resistive paint, ceramic, doped glass and ion-implanted material.

28. The system of claim 27, wherein resistance of said material is in the range of $10^2 \leq \text{ohms/square} \leq 10^{14}$.

29. The system of claim 28, wherein said range is within: $10^7 \leq \text{ohms/square} \leq 10^{11}$.

30. A method for controlling ion behavior in an ion-based analysis system, said method including the steps of:
   providing a flow path for a flow of ions,
   generating an ion filter field in said flow path for filtering said flow of ions,
   controlling behavior of ions in said flow of ions,
   separating ions in said flow of ions according to species, said separating being based on ion-mobility-based behavior of said ions in said filter field, and
   controlling actively a control structure for reducing field artifacts in said flow path, said control structure being recessed to reduce the effect of charge buildup upon said flow of ions.

31. The method of claim 30, including the step of generating an influencing field that influences said flow of ions to be separated.

32. The method of claim 31, wherein said influencing includes taking an action selected from the group consisting of focusing, trapping, confining, translating, selecting, and filtering ions in said flow path.

33. The method of claim 32, wherein said filter field is a compensated asymmetric high-low varying RF filter field.

34. The method of claim 33, wherein said system is operated to determine the time of flight of ions passing along said flow path.

35. The method of claim 30, including the step of providing said control structure with a charge-dissipating control material in said flow path, wherein said control material is coupled to said system to prevent charge buildup in said flow path.

36. The method of claim 30, wherein said control structure includes an array of electrodes.

37. The method of claim 30, wherein said control structure is recessed to minimize the effect of charge buildup upon said flow of ions.

38. The method of claim 30, wherein said recess is formed by the mouth of a flow channel.

39. The method of claim 38, wherein said flow channel introduces a gas flow into said flow of ions for concentrating said flow of ions.

40. The method of claim 39 including the step of introducing a plurality of gas flows into said flow of ions for concentrating said flow of ions in said flow path.

41. The method of claim 36 including the step of isolating said array from said filter electrodes.

42. The method of claim 36, wherein said array is partially conducting and is coupled to said system for dissipating charge build-up in said flow path.

* * * * *